United States Patent
Ohyama et al.

(10) Patent No.: US 10,139,220 B2
(45) Date of Patent: Nov. 27, 2018

(54) THREE-DIMENSIONAL MEASUREMENT DEVICE

(71) Applicant: CKD Corporation, Aichi (JP)

(72) Inventors: Tsuyoshi Ohyama, Aichi (JP);
Norihiko Sakaida, Aichi (JP);
Takahiro Mamiya, Aichi (JP);
Hiroyuki Ishigaki, Aichi (JP)

(73) Assignee: CKD Corporation, Aichi (JP)

( * ) Notice: Subject to any disclaimer, the term of this patent is extended or adjusted under 35 U.S.C. 154(b) by 0 days.

(21) Appl. No.: 15/867,821

(22) Filed: Jan. 11, 2018

(65) Prior Publication Data

US 2018/0135975 A1    May 17, 2018

Related U.S. Application Data

(63) Continuation of application No. PCT/JP2016/050553, filed on Jan. 8, 2016.

(30) Foreign Application Priority Data

Jul. 14, 2015    (JP) ................................. 2015-140225

(51) Int. Cl.
| | | |
|---|---|---|
| G01B 11/25 | (2006.01) | |
| G01N 21/95 | (2006.01) | |
| G06T 1/00 | (2006.01) | |

(52) U.S. Cl.
CPC ...... G01B 11/2513 (2013.01); G01B 11/2504 (2013.01); G01B 11/2527 (2013.01); G01N 21/9501 (2013.01); G06T 1/00 (2013.01)

(58) Field of Classification Search
CPC ............ G01B 11/2513; G01B 11/2504; G01B 11/0608; G01B 11/14; G01B 2210/56; G01N 21/9501
See application file for complete search history.

(56) References Cited

U.S. PATENT DOCUMENTS

| 9,243,899 B2 * | 1/2016 | Jeong ................. G01B 11/0608 |
| 2010/0091302 A1 * | 4/2010 | Kim .................... G01B 11/2531 356/603 |
| 2010/0295941 A1 * | 11/2010 | Jeong ................. G01B 11/2531 348/135 |

(Continued)

FOREIGN PATENT DOCUMENTS

JP    2013-124937 A    6/2013

*Primary Examiner* — Sang Nguyen
(74) *Attorney, Agent, or Firm* — Osha Liang LLP

(57) ABSTRACT

A three-dimensional measurement device includes: a first irradiator that radiates a first light pattern from a first position toward an object; a first grid controller that controls a first grid to change phases of the first light pattern; a second irradiator that radiates a second light pattern from a second position toward the object; a second grid controller that controls the second grid to change phases of the second light pattern; a camera that takes an image of reflected light from the object; and a processor that: performs one of a first imaging process of imaging processes performed by radiation of the first light pattern and a second imaging process of imaging processes performed by radiation of the second light pattern; and subsequently performs the other imaging process without waiting for completion of the transfer or changeover of the first or the second grid involved in the one imaging process.

20 Claims, 8 Drawing Sheets

(56) References Cited

U.S. PATENT DOCUMENTS

2013/0147778 A1* 6/2013 Ninan ................... G09G 3/3426
    345/207
2013/0286408 A1* 10/2013 Castillo ................ G01B 11/272
    356/610
2014/0009601 A1* 1/2014 Cho ................... G01B 11/0608
    348/126

* cited by examiner

| DATA DISTRICT (V) | FREQUENCY (NUMBER) |
|---|---|
| $-1.0 \sim -0.9$ | 51 |
| $\sim -0.8$ | 22 |
| $\sim -0.7$ | 18 |
| $\sim -0.6$ | 16 |
| $\sim -0.5$ | 14 |
| $\sim -0.4$ | 12 |
| $\sim -0.3$ | 12 |
| $\sim -0.2$ | 12 |
| $\sim -0.1$ | 12 |
| $\sim 0$ | 11 |
| $\sim 0.1$ | 11 |
| $\sim 0.2$ | 12 |
| $\sim 0.3$ | 12 |
| $\sim 0.4$ | 12 |
| $\sim 0.5$ | 14 |
| $\sim 0.6$ | 12 |
| $\sim 0.7$ | 16 |
| $\sim 0.8$ | 18 |
| $\sim 0.9$ | 22 |
| $\sim 1$ | 51 |

THREE-DIMENSIONAL MEASUREMENT DEVICE

BACKGROUND OF THE INVENTION

Technical Field

The present disclosure relates to a three-dimensional measurement device configured to perform three-dimensional measurement by using the phase shift method.

Background

In general, when electronic components are to be mounted on a printed circuit board, solder paste is printed on a predetermined electrode pattern provided on a printed circuit board. The electronic components are then temporarily fastened on the printed circuit board by means of the viscosity of the solder paste. The printed circuit board is subsequently introduced into a reflow furnace and is subjected to a predetermined reflow process to achieve soldering. Recently there has been a need to inspect the printing condition of solder paste in a stage prior to introduction into the reflow furnace. A three-dimensional measurement device may be used for this inspection.

Various contactless three-dimensional measurement devices have been proposed recently. For example, techniques regarding three-dimensional measurement devices using the phase shift method have been proposed.

In a three-dimensional measurement device using the phase shift method, a measurement object (solder paste in this case) is irradiated with a light pattern emitted from an irradiator configured by a combination of a light source configured to emit a predetermined light and a grid configured to convert the light emitted from the light source into a light pattern having a sinusoidal (striped) light intensity distribution. Points on the substrate are observed with an imaging unit placed immediately above the substrate. The imaging unit may be, for example, a CCD camera including a lens, an imaging element and the like.

In the configuration described above, an intensity (luminance) I of the light at each pixel on image data taken by the imaging unit is given by Expression (U1) given below:

$$I = f \cdot \sin \varphi + e \quad (U1)$$

where f denotes a gain, e denotes an offset and $\varphi$ denotes a phase of the light pattern.

The phase of the light pattern is changed in, for example four different stages ($\varphi+0$, $\varphi+90°$, $\varphi+180°$ and $\varphi+270°$) by transfer or changeover control of the above grid, and image data having intensity distributions $I_0$, $I_1$, $I_2$ and $I_3$ corresponding to these phases are taken. The phase $\varphi$ is determined by cancelling out f (gain) and e (offset) according to Expression (U2) given below:

$$\varphi = \tan^{-1}[(I_1 - I_3)/(I_2 - I_0)] \quad (U2)$$

A height (Z) at each coordinates (X,Y) on a measurement object is determined by using this phase $\varphi$, based on the principle of triangulation.

In a configuration equipped with the above irradiator at only one location, the measurement object is likely to have a shadow part that is not irradiated with the light pattern. The shadow part is unlikely to be measured appropriately.

By taking into account the foregoing, in order to enhance the measurement accuracy and the like, a known technique performs measurement by radiation light patterns from two different directions. Additionally, in order to shorten the measurement time and the like, a recently proposed technique performs a first imaging process that is one time of imaging process among a plurality of imaging processes performed by radiation of a first light pattern from a first irradiator, subsequently performs a second imaging process that is one time of imaging process among a plurality of imaging processes performed by radiation of a second light pattern from a second irradiator, and simultaneously performs transfer or changeover processes of both the first and second irradiators after completion of both the first and second imaging processes (as described in, for example, Patent Literature 1).

CITATION LIST

Patent Literature

PTL 1: JP 2013-124937A

SUMMARY OF THE INVENTION

In the prior art three-dimensional measurement device using the phase shift method, however, there is a need to change the phase of the radiated light pattern in four different stages (or three different stages) and to take four different (or three different) images. In the case of radiation of light patterns from two different directions, four (or three) imaging processes with each light pattern are required with regard to one measurement object area. This requires a total of eight (or six) imaging processes and is likely to increase the imaging time.

Imaging with a camera or the like is generally performed in a relatively short time period (for example, 2 msec), since imaging under intensive illumination in a shorter time period decreases the effect of mechanical vibrations. It takes a relatively long time (for example, 20 msec) to transfer a grid of the irradiator, in order to avoid vibrations and the like. When a liquid crystal grid or the like is employed as the grid, it also takes a relatively long time to complete its changeover control.

In the configuration of the above Patent Literature 1 that performs a total of eight imaging processes under the two light patterns (four processes with each light pattern) with regard to a predetermined measurement object area, on the assumption that the imaging time required for each imaging process is [2 msec] and the time required for each transfer or the like of the grid is [20 msec], as shown in FIG. 10, the time period required for completion of all imaging processes (last imaging process) with regard to the predetermined measurement object area is [time period required for the first imaging process [2 ms]×4 times]+[time period required for the second imaging process [2 ms]×4 times]+[time period required for transfer or the like of the first grid and the second grid [20 ms]×3 times]=total of [76 msec].

When a large number of measurement object areas are set on a single printed circuit board, a several-fold time period is required for measurement of the single printed circuit board. There is accordingly a need for further shortening the measurement time.

The above characteristics may be found in the fields of not only the height measurement of the solder paste printed on the printed circuit board but other three-dimensional measurement devices.

By taking into account the circumstances described above, one or more embodiments of the invention provide a three-dimensional measurement device that allows for three-dimensional measurement by the phase shift method with the higher accuracy in the shorter time period.

The following describes each of various aspects provided adequately to solve the problems described above. Functions and advantageous effects that are characteristic of each of the aspects are also described as appropriate.

Aspect 1. There is provided a three-dimensional measurement device comprising a first irradiator that includes a first light source configured to emit a predetermined light and a first grid configured to convert the light from the first light source into a first light pattern having a striped light intensity distribution, and that is configured to radiate the first light pattern from a first position toward a measurement object; a first grid controller configured to control transfer or changeover of the first grid, such as to change a phase of the first light pattern radiated by the first irradiator in a predetermined first number of ways (for example, "3" or "4" different ways); a second irradiator that includes a second light source configured to emit a predetermined light and a second grid configured to convert the light from the second light source into a second light pattern having a striped light intensity distribution, and that is configured to radiate the second light pattern from a second position that is different from the first position toward the measurement object; a second grid controller configured to control transfer and changeover of the second grid, such as to change a phase of the second light pattern radiated by the second irradiator in a predetermined second number of ways (for example, "2" or "3" different ways), which is smaller than the predetermined first number of ways; an imaging unit configured to take an image of reflected light from the measurement object that is irradiated with the first light pattern or the second light pattern; and an image processor configured to perform three-dimensional measurement of the measurement object by a phase shift method, based on image data taken by the imaging unit.

The three-dimensional measurement device is configured to perform one imaging process out of a first imaging process that is one time of imaging process among the predetermined first number of imaging processes performed by radiation of the first light pattern with changing the phase in the predetermined first number of ways, and a second imaging process that is one time of imaging process among the predetermined second number of imaging processes performed by radiation of the second light pattern with changing the phase in the predetermined second number of ways, and subsequently perform the other imaging process out of the first and the second imaging processes without waiting for completion of a transfer or changeover process of the first grid or the second grid involved in the one imaging process (including before a start of the transfer or changeover process).

The image processor comprises a first measurement unit configured to perform three-dimensional measurement of the measurement object, based on the predetermined first number of image data taken by the predetermined first number of the first imaging processes; a second measurement unit configured to perform three-dimensional measurement of the measurement object, based on the predetermined second number of image data taken by the predetermined second number of the second imaging processes, by using a relationship between a gain and an offset that is determined according to a predetermined imaging condition and a value of the gain or the offset with regard to each pixel on the image data that is determined from a luminance value of the pixel; and a measurement value acquirer configured to obtain a measurement result of one measurement unit (for example, measurement result of the first measurement unit) out of the first and the second measurement units that uses one light pattern (for example, first light pattern) out of the first and the second light patterns with regard to a region that is measurable by radiation of the one light pattern, as a measurement value of the region, and obtain a measurement result of the other measurement unit (for example, measurement result of the second measurement unit) that uses the other light pattern (for example, second light pattern) out of the first and the second light patterns with regard to a region that has difficulty in measurement by radiation of the one light pattern (for example, a region having an insufficient luminance or a region in which appropriate height data is unobtainable), as a measurement value of the region.

The configuration of the above aspect 1 suppresses generation of any shadow part of the measurement object that is not irradiated with the light pattern by radiation of the light patterns from two different directions. With regard to a region that is measurable by radiation of, for example, the first light pattern out of the two light patterns, the configuration of this aspect obtains the measurement result of the first measurement unit using the first light pattern, as the measurement result of this region. When regard to a region that has difficulty in measurement by radiation of the first light pattern, on the other hand, the configuration of this aspect obtains the measurement result of the second measurement unit using the other second light pattern, as the measurement result of this region. This accordingly obtains measurement data without deficiency of data. As a result, this enhances the measurement accuracy.

Additionally, after performing one imaging process (for example, first imaging process) out of one time of the first imaging process under the first light pattern and one time of the second imaging process under the second light pattern, the configuration of this aspect performs the other imaging process (for example, second imaging process) out of the first and the second imaging processes without waiting for completion of transfer or the like of the grid involved in the one imaging process.

The configuration that performs imaging with the other grid and transfer or the like of the other grid after this imaging without waiting for completion of transfer or the like of one grid enables transfer processes of the two grids that require a relatively long time period to be performed in a partly overlapping manner. As a result, this shortens the time period required for completion of all imaging processes (last imaging process) with regard to a predetermined measurement object area.

Furthermore, according to this aspect, measurement based on radiation of the second light pattern is configured to perform three-dimensional measurement of the measurement object by using the relationship between the gain A and the offset B [for example, A=K (proportional constant)×B] determined according to a predetermined imaging condition and the value of a gain A(x,y) or an offset B(x,y) with regard to each pixel (x,y) determined from a luminance value V(x,y) of the pixel (x,y) on the image data.

This configuration allows for three-dimensional measurement by the phase shift method by obtaining only at least two different image data taken under the second light pattern with changing the phase in at least two different ways. This results in reducing the required number of images taken under the second light pattern (number of imaging processes), compared with the required number of images taken under the first light pattern.

For example, when four different (or three different) images are taken with radiation of the first light pattern with changing the phase in four different ways (or three different ways) and two different images are taken with radiation of the second light pattern with changing the phase in two different ways, the total number of imaging processes is six times (or five times). This reduces the imaging time.

Accordingly, compared with the prior art technique, this configuration requires the less total number of imaging processes and shortens the imaging time. As a result, this ensures measurement with the higher accuracy in the shorter time period.

The light emitted from the light source is attenuated when passing through the grid, is subsequently attenuated when being reflected by the measurement object, is lastly attenuated during A/D conversion (along to digital conversion) in the imaging unit, and is then obtained as a luminance value of each pixel in the image data.

The luminance value of each pixel in the image data taken by the imaging unit may thus be expressed by, for example, multiplying the brightness (luminance) of the light source, the attenuation rate when the light emitted from the light source passes through the grid, the reflectance when the light is reflected by the measurement object and the conversion efficiency during A/D conversion (analog to digital conversion) in the imaging unit.

For example, a brightness of the light source (uniform light) is represented by L; and a transmittance of the grid is expressed as $G=\alpha \sin\theta+\beta$, where $\alpha$ and $\beta$ denote arbitrary constants.

A reflectance at coordinates (x,y) of the measurement object is represented by R(x,y); a conversion efficiency of each pixel of the imaging unit (imaging element) is represented by E; a luminance value of a pixel on an image corresponding to the coordinates (x,y) on the measurement object is represented by V(x,y); a gain of the light pattern at the coordinates (x,y) on the measurement object is represented by A(x,y); and an offset of the light pattern at the coordinates (x,y) on the measurement object is represented by B(x,y). In this case, the luminance value of each pixel may be expressed by Expression (F1) given below:

[Math. 1]

$$V(x, y) = L \times G \times R(x, y) \times E \quad (F1)$$
$$= A(x, y)\sin\theta + B(x, y)$$

The gain A(x,y) may be expressed by a difference between a luminance value $V(x,y)_{MAX}$ with light of "$\sin\theta=1$" and a luminance value $V(x,y)_{MIN}$ with light of "$\sin\theta=-1$". For example, when a transmittance of the grid at $\theta=0$ (=average transmittance) is represented by $G\theta_{=0}$, a transmittance of the grid at $\theta=\Pi/2$ (=maximum transmittance) is represented by $G\theta_{=\Pi/2}$, and a transmittance of the grid at $\theta=-\Pi/2$ (=minimum transmittance) is represented by $G\theta_{=-\Pi/2}$, the gain A(x,y) may be expressed by Expression (F2) given below:

[Math. 2]

$$A(x, y) = \{(L \times G_{\theta=\pi/2} \times R(x, y) \times E) - (L \times G_{\theta=-\pi/2} \times R(x, y) \times E)\}/2 \quad (F2)$$
$$= \{(L \times R(x, y) \times E) \times (G_{\theta=\pi/2} - G_{\theta=-\pi/2})\}/2$$

The offset B(x,y) is equal to a luminance value V(x,y) with light of "$\sin\theta=0$" and is an average value of the luminance value $V(x,y)_{MAX}$ with the light of "$\sin\theta=1$" and the luminance value $V(x,y)_{MIN}$ with the light of "$\sin\theta=-1$". The offset B(x,y) may be expressed by Expression (F3) given below:

[Math. 3]

$$B(x, y) = L \times G_{\theta=0} \times R(x, y) \times E \quad (F3)$$
$$= \{(L \times G_{\theta=\pi/2} \times R(x, y) \times E) + (L \times G_{\theta=-\pi/2} \times R(x, y) \times E)\}/2$$
$$= \{(L \times R(x, y) \times E) \times (G_{\theta=\pi/2} + G_{\theta=-\pi/2})\}/2$$

The maximum value $V(x,y)_{MAX}$, the minimum value $V(x,y)_{MIN}$ and the average value $V(x,y)_{AV}$ of the luminance value may be respectively expressed by Expressions (F4), (F5) and (F6) given below and provide such a relationship as that shown in the graph of FIG. 4.

[Math. 4]

$$V(x,y)_{MAX}=(L\times G_{\theta=\pi/2}\times R(x,y)\times E)=B(x,y)+A(x,y) \quad (F4)$$

$$V(x,y)_{MIN}=(L\times G_{\theta=-\pi/2}\times R(x,y)\times E)=B(x,y)-A(x,y) \quad (F5)$$

$$V(x,y)_{AV}=(L\times R(x,y)\times E)\times(G_{\theta=\pi/2}+G_{\theta=-\pi/2})/2=B(x,y) \quad (F6)$$

As understood from FIG. 4, the average value $V(x,y)_{AV}$ of the maximum value $V(x,y)_{MAX}$ of the luminance value and the minimum value $V(x,y)_{MIN}$ of the luminance value at predetermined coordinates (x,y) is equal to the offset B(x,y). The difference between the offset B(x,y) and the maximum value $V(x,y)_{MAX}$ and the difference between the offset B(x,y) and the minimum value $V(x,y)_{MIN}$ are respectively given as the gain A(x,y).

The luminance value V(x,y) changes in proportion to the brightness L or the reflectance R(x,y) of the light source. The value of the gain A or the offset B is accordingly halved, for example, at a coordinate position having half the reflectance R.

Expression (F7) given below is derived by substituting Expressions (F2) and (F3) given above with Expressions (F2') and (F3') given below and collectively reorganizing these Expressions (F2') and (F3'):

[Math. 5]

$$2A(x,y)/(G_{\theta=\pi/2}-G_{\theta=-\pi/2})=(L\times R(x,y)\times E) \quad (F2')$$

$$2B(x,y)/(G_{\theta=\pi/2}+G_{\theta=-\pi/2})=(L\times R(x,y)\times E) \quad (F3')$$

$$2A(x,y)/(G_{\theta=\pi/2}-G_{\theta=-\pi/2})=2B(x,y)/(G_{\theta=\pi/2}+G_{\theta=-\pi/2}) \quad (F7)$$

Additionally, Expression (F8) given below is derived by solving Expression (F7) given above with regard to A(x,y) and is expressed as shown in the graph of FIG. 5.

[Math. 6]

$$A(x, y) = B(x, y) \times (G_{\theta=\pi/2} - G_{\theta=-\pi/2})/(G_{\theta=\pi/2} + G_{\theta=-\pi/2}) \quad (F8)$$
$$= K \times B(x, y)$$

where
proportional constant $K=(G_{\theta=\pi/2}-G_{\theta=-\pi/2})/(G_{\theta=\pi/2}+G_{\theta=-\pi/2})$ Changing one of the brightness L and the reflectance R(x,y) of the light source while fixing the other increases or decreases the offset B(x,y) and also increases or decreases the gain A(x,y) in proportion to the offset B(x,y). According to this Expression (F8), the other of the gain A and the offset B is determinable by determining one of the gain A and the offset B. The proportional constant K is determined according to the transmittance G of the grid, independently of the brightness L and the reflectance R of the light source. This may be expressed as Aspects 2 and 3 described below.

The configuration that simultaneously radiates two light patterns having mutually different wavelength components (RGB components) and separately takes images of respective light components of reflected light from a measurement object that is irradiated with these two light patterns as described in the above Patent Literature 1 enables the first imaging process and the second imaging process to be performed simultaneously and further shortens the measurement time. This configuration, however, requires, for example, a color camera equipped with a plurality of dichromic mirrors and a plurality of imaging units corresponding to respective wavelength regions or a single plate-type color camera that differs a wavelength region that allows for imaging with regard to each pixel, as a camera that separately takes images of the respective light components. This is likely to require a very expensive measurement device. The light patterns of the respective RGB components have different reflectances at a measurement object. The respective light patterns are thus likely to have different measurement accuracies, depending on the types of colors of the measurement object.

Aspect 2: In the three-dimensional measurement device described in Aspect 1 above, the relationship between the gain and the offset may be a relationship that mutually unequivocally determines the gain and the offset.

When the relationship between the gain A and the offset B is a relationship that mutually unequivocally determines the gain A and the offset B, the offset B may be determinable according to the gain A or the gain A may be determinable according to the offset B by referring to, for example, a numerical table or table data provided to indicate the relationship between the gain A and the offset B.

Aspect 3: In the three-dimensional measurement device described in Aspect 1 above, the relationship between the gain and the offset may be a relationship that gives the gain and the offset proportional to each other.

When the relationship between the gain and the offset is a relationship that gives the gain and the offset proportional to each other, the offset B may be determinable from the gain A or the gain A may be determinable from the offset B by referring to, for example, a relational expression such as $A=K \times B+C$ (where C denotes dark current (offset) of the camera). This may be implemented by such a configuration as that of Aspect 4 described below.

Aspect 4: In the three-dimensional measurement device described in any of Aspects 1 to 3 above, when the predetermined second number is equal to 2, the second measurement unit calculates a phase $\theta$ that satisfies relations of Expressions (1), (2) and (3) given below in three-dimensional measurement:

$$V_0 = A \sin \theta + B \quad (1)$$

$$V_1 = A \sin(\theta + \gamma) + B \quad (2)$$

$$A = KB \quad (3)$$

where $\theta$ and $\gamma$ respectively denote relative phases of the second light pattern with changing the phase in two different ways; $V_0$ and $V_1$ respectively denote luminance values of each pixel in two different image data, $\gamma \neq 0$, A denotes the gain, B denotes the offset and K denotes a proportional constant.

In the above configuration of Aspect 4, Expression (4) given below is derived by substituting Expression (3) given above into Expression (1) given above:

$$V_0 = KB \sin \theta + B \quad (4)$$

Expression (5) given below is derived by solving Expression (4) with regard to the offset B:

$$B = V_0/(K \sin \theta + 1) \quad (5)$$

Expression (6) given below is derived by substituting Expression (3) given above into Expression (2) given above:

$$V_1 = KB \sin(\theta + \gamma) + B \quad (6)$$

Expression (7) given below is derived by substituting Expression (6) given above into Expression (5) given above and reorganizing the expression as shown by [Math. 7] given below:

[Math. 7]

$$\begin{aligned} V_1 &= K \times \{V_0/(K\sin\theta+1)\}\sin(\theta+\gamma) + \{V_0/(K\sin\theta+1)\} \\ V_1 &\times (K\sin\theta+1) = KV_0\sin(\theta+\gamma) + V_0 \\ &= KV_0\{\sin\theta\cos\gamma + \sin\gamma\cos\theta\} + V_0 \\ &- V_1 K\sin\theta + KV_0\cos\gamma\sin\theta + KV_0\sin\gamma\cos\theta + V_0 - V_1 = 0 \\ K(V_0\cos\gamma - V_1)\sin\theta + KV_0\sin\gamma\cos\theta + (V_0-V_1) = 0 \\ (V_0\cos\gamma - V_1)\sin\theta + V_0\sin\gamma\cos\theta + (V_0-V_1)/K = 0 \end{aligned} \quad (7)$$

Expression (7) given above may be rewritten as Expression (8) given below when "$V_0 \cos \gamma - V_1 = a$", "$V_0 \sin \gamma = b$" and "$(V_0 - V_1)/K = c$":

$$a \sin \theta + b \cos \theta + c = 0 \quad (8)$$

Expression (9) shown by [Math. 9] given below is derived by solving Expression (8) given above with regard to the phase $\theta$ as shown by [Math. 8] given below:

[Math. 8]

$$\frac{a}{b}\sin\theta + \sqrt{1-\sin^2\theta} + \frac{c}{b} = 0$$

$$\sqrt{1-\sin^2\theta} = -\frac{1}{b}(c + a\sin\theta)$$

$$1 - \sin^2\theta = \frac{1}{b^2}(c^2 + 2ac\sin\theta + a^2\sin^2\theta)$$

$$b^2 - b^2\sin^2\theta = c^2 + 2ac\sin\theta + a^2\sin^2\theta$$

$$(a^2 + b^2)\sin^2\theta + 2ac\sin\theta + c^2 = 0$$

$$\sin\theta = \frac{-ac \pm \sqrt{a^2c^2 - (a^2+b^2)(c^2-b^2)}}{a^2+b^2}$$

$$\theta = \sin^{-1}\left[\frac{-ac \pm \sqrt{a^2c^2 - (a^2+b^2)(c^2-b^2)}}{a^2+b^2}\right]$$

[Math. 9]

$$\theta = \sin^{-1}\left[\frac{-ac \pm b\sqrt{a^2+b^2-c^2}}{a^2+b^2}\right] \quad (9)$$

where
$a = V_0 \cos \gamma - V_1$
$b = V_0 \sin \gamma$
$c = (V_0 - V_1)/K$

The configuration of "calculating the phase $\theta$ that satisfies relations of Expressions (1), (2) and (3)" in Aspect 4 described above may thus be regarded as the configuration of "calculating the phase $\theta$ according to Expression (9)".

The algorithm for obtaining the phase θ is not necessarily limited to Expression (9) given above, but any other configuration that satisfies the relations of Expressions (1), (2) and (3) given above may be employed.

Taking into account the dark current C of the camera described above and the like may further enhance the measurement accuracy.

Aspect 5: In the three-dimensional measurement device described in Aspect 4 above, γ may be equal to 180 degrees.

The configuration of this Aspect 5 causes two imaging processes to be performed under the second light pattern of two different phases that differ by 180 degrees.

Expression (10) given below is derived by substituting γ=180 degrees in Expression (2) given above:

$$V_1 = A\sin(\theta + 180°) + B \quad (10)$$
$$= -A\sin\theta + B$$

Expression (11) given below is derived from Expressions (1) and (10) given above, and Expression (12) given below is derived by solving Expression (11) with regard to the offset B:

$$V_0 + V_1 = 2B \quad (11)$$

$$B = (V_0 + V_1)/2 \quad (12)$$

Additionally, Expression (13) given below is derived by substituting Expression (12) given above into Expression (3) given above:

$$A = KB \quad (13)$$
$$= K(V_0 + V_1)/2$$

Expression (1') given below is obtained by rearranging Expression (1) given above with regard to "sin θ":

$$\sin\theta = (V_0 - B)/A \quad (1')$$

Expression (14) given below is derived by substituting Expressions (12) and (13) given above into Expression (1') given above:

$$\sin\theta = \{V_0 - (V_0 + V_1)/2\}/\{K(V_0 + V_1)/2\} \quad (14)$$
$$= (V_0 - V_1)/K(V_0 + V_1)$$

Expression (15) given below is derived by solving Expression (14) given above with regard to the phase θ:

$$\theta = \sin^{-1}[(V_0 - V_1)/K(V_0 + V_1)] \quad (15)$$

The phase θ may thus be specified by the known luminance values $V_0$ and $V_1$ and the constant K.

As described above, the above configuration of Aspect 5 enables the phase θ to be determined by a relatively simple arithmetic expression and further increases the processing speed in three-dimensional measurement of the measurement object.

Aspect 6: In the three-dimensional measurement device described in Aspect 4 above, γ may be equal to 90 degrees.

The configuration of this Aspect 6 causes two imaging operations to be performed under the second light pattern of two different phases that differ by 90 degrees.

Expression (16) given below is derived by substituting γ=90 degrees in Expression (2) given above:

$$V_1 = A\sin(\theta + 90°) + B \quad (16)$$
$$= A\cos\theta + B$$

Expression (17) given below is derived by rearranging Expression (16) given above with regard to "cos θ":

$$\cos\theta = (V_1 - B)/A \quad (17)$$

As described above, Expression (1') given below is obtained by rearranging Expression (1) given above with regard to "sin θ":

$$\sin\theta = (V_0 - B)/A \quad (1')$$

Expression (19) given below is derived by substituting Expressions (1') and (17) given above into Expression (18) given below, and Expression (20) given below is derived by rearranging this Expression (19):

$$\sin^2\theta + \cos^2\theta = 1 \quad (18)$$

$$\{(V_0 - B)/A\}^2 + \{(V_1 - B)/A\}^2 = 1 \quad (19)$$

$$(V_0 - B)^2 + (V_1 - B)^2 = A^2 \quad (20)$$

Expression (21) given below is derived by substituting Expression (3) given above into Expression (20) given above, and Expression (22) given below is derived by rearranging this Expression (21):

$$(V_0 - B)^2 + (V_1 - B)^2 = K^2 B^2 \quad (21)$$

$$(2 - K^2)B^2 - 2(V_0 + V_1)B + V_0^2 V_1^2 = 0 \quad (22)$$

Expression (23) given below is derived by solving Expression (22) given above with regard to the offset B:

[Math. 10]

$$B = (V_0 + V_1) - \sqrt{(V_0 + V_1)^2 - (2 - K^2)V_0^2 V_1^2} \quad (23)$$

where B>0

The offset B may thus be specified by the known luminance values $V_0$ and $V_1$ and the constant K.

Expression (25) given below is derived by substituting Expressions (1') and (17) given above into Expression (24) given below, and Expression (26) given below is derived by rearranging this Expression (25):

$$\tan\theta = \sin\theta/\cos\theta \quad (24)$$
$$= \{(V_0 - B)/A\}/\{(V_1 - B)/A\} \quad (25)$$
$$= (V_0 - B)/(V_1 - B) \quad (26)$$

Expression (27) given below is derived by solving Expression (26) given above with regard to the phase θ:

$$\theta = \tan^{-1}\{(V_0 - B)/(V_1 - B)\} \quad (27)$$

The phase θ may thus be specified by the known luminance values $V_0$ and $V_1$ and the constant K according to Expression (23) given above.

As described above, the above configuration of Aspect 6 enables the phase θ to be determined by an arithmetic expression using "$\tan^{-1}$". This allows for measurement of the height in the range of 360 degrees from −180 degrees to 180 degrees and further expands the measurement range.

Aspect 7. The three-dimensional measurement device described in any of Aspects 1 to 6 above may further comprise a storage unit configured to store the relationship between the gain and the offset that is calculated in advance by calibration.

For example, the gain A and the offset B with regard to each pixel may be specified, based on three different or four different image data taken by irradiating a reference plate with a light pattern with changing the phase in three different ways or in four different ways, and the constant K may be determined according to Expression (3) given above. The configuration of Aspect 7 above accordingly ensures height measurement with the higher accuracy with respect to each pixel.

Aspect 8. The three-dimensional measurement device described in any of Aspects 1 to 6 above may further comprise a relationship grasping unit configured to grasp the relationship between the gain and the offset, based on the predetermined first number of image data taken by the predetermined first number of the first imaging processes.

The configuration of Aspect 8 has similar functions and advantageous effects to those of the configuration of Aspect 7 described above. As described above, the relationship between the gain A and the offset B (proportional constant K) is determined according to the transmittance G of the grid, independently of the brightness L and the reflectance R of the light source. When identical grids are used as the first grid and the second grid, the relationship between the gain and the offset in the first irradiator is identical with the relationship between the gain and the offset in the second irradiator. Using this fact saves the labor of calibration that is performed in Aspect 7 above and further shortens the measurement time.

Aspect 9. The three-dimensional measurement device described in any of Aspects 1 to 6 above may further comprise a relationship grasping unit configured to grasp the relationship between the gain and the offset, based on the predetermined second number of image data taken by the predetermined second number of the second imaging processes.

For example, the configuration of this aspect determines the values of the offset B with regard to all the pixels of the image data using, for example, Expression (12) given above, extracts luminance values V of the pixels having an identical value of the offset B among them and creates a histogram of the extracted luminance values. The configuration then determines a maximum value $V_{MAX}$ and a minimum value $V_{MIN}$ of the luminance value from the histogram.

As described above, the offset B is the average value of the maximum value $V_{MAX}$ and the minimum value $V_{MIN}$ of the luminance value, and the gain A is half the difference between the maximum value $V_{MAX}$ and the minimum value $V_{MIN}$. This enables the constant K to be determined according to Expression (3) given above. The configuration of Aspect 9 above saves the labor of calibration that is performed in Aspect 7 described above and further shortens the measurement time.

Aspect 10. In the three-dimensional measurement device described in any of Aspects 1 to 9 above, the measurement value acquirer may obtain a measurement result of the first measurement unit with regard to a region that is measurable by radiation of the first light pattern, as a measurement value of the region, and obtain a measurement result of the second measurement unit using the other second light pattern with regard to a region that has difficulty in measurement by radiation of the first light pattern, as a measurement value of the region.

The number of the first imaging processes is larger than the number of the second imaging processes, so that the measurement result of the first measurement unit has the higher measurement accuracy than the measurement result of the second measurement unit. By taking into account this fact, the configuration of Aspect 10 above mainly uses the measurement result of the first measurement unit having the higher measurement accuracy, while using the measurement result of the second measurement unit with regard to partial deficiency of data. This accordingly obtains measurement data having high measurement accuracy and little deficiency of data as a whole Aspect 11. The three-dimensional measurement device described in any of Aspects 1 to 10 above may be configured to start a transfer or changeover process of the first grid that is involved in the first imaging process, simultaneously with termination of the first imaging process. The three-dimensional measurement device may be configured to start the first imaging process simultaneously with termination of the transfer or changeover process of the first grid. The three-dimensional measurement device may be configured to perform the second imaging process during the transfer or changeover process of the first grid.

The configuration of Aspect 11 above enables all the first imaging processes with regard to the predetermined measurement object area to be completed in the shortest possible time period. The number of the second imaging processes is smaller than the number of the first imaging processes. The configuration that performs the second imaging process during the transfer or changeover process of the first grid (between one time of the first imaging process and a subsequent time of the first imaging process) enables all the second imaging processes to be completed, while all the first imaging processes with regard to the predetermined measurement object area are completed. As a result, this configuration further enhances the functions and the advantageous effects of Aspect 1 described above and further shortens the measurement time.

Aspect 12. The three-dimensional measurement device described in any of Aspects 1 to 11 above may be configured to perform at least a transfer or changeover process of the second grid, simultaneously with a transfer or changeover process of the first grid.

In a configuration that radiates a light pattern from the other irradiator for imaging during transfer or the like of the grid in one irradiator out of the two irradiators, the effects of a mechanical vibration during transfer of the grid by means of an actuator or the like and an electric noise possibly generated during changeover control of a liquid crystal shutter or the like included in the grid are likely to generate a measurement error or the like.

The configuration of Aspect 12 above, however, does not perform transfer or the like of the second grid of the second irradiator during the first imaging process. This suppresses reduction in the measurement accuracy of the first measurement unit.

The configuration of Aspect 12 above is allowed to perform the second imaging process during the transfer or changeover process of the first grid of the first irradiator. As described above, the measurement by the second measurement unit originally has the lower measurement accuracy than the measurement by the first measurement unit. Even when a measurement error or the like is generated, the effect of this measurement error on the measurement result is smaller than the effect of a measurement error on the measurement result by the first measurement unit.

Especially, in the configuration of Aspect 10 or Aspect 11 above, the measurement result of the second measurement unit serves as complementary data to complement the deficiency of data in the measurement result of the first measurement unit. The decrease in measurement accuracy of this measurement result has extremely small effect on the entire measurement data.

Aspect 13. In the three-dimensional measurement device described in any of Aspects 1 to 12 above, the measurement object may be either a solder paste printed on a printed circuit board or a solder bump formed on a wafer substrate.

This configuration of Aspect 13 above allows for measurement of the height of, for example, the solder paste printed on the printed circuit board or the solder bump formed on the wafer substrate. This configuration also enables the good/poor quality of the solder paste or the solder bump to be determined, based on the measurement value in inspection of the solder paste or the solder bump. This configuration accordingly ensures the functions and the advantageous effects of the respective aspects described above in this inspection and allows for the good/poor quality determination with high accuracy. This results in improving the inspection accuracy in a solder printing inspection apparatus or in a solder bump inspection apparatus.

DETAILED DESCRIPTION

Figure 1:
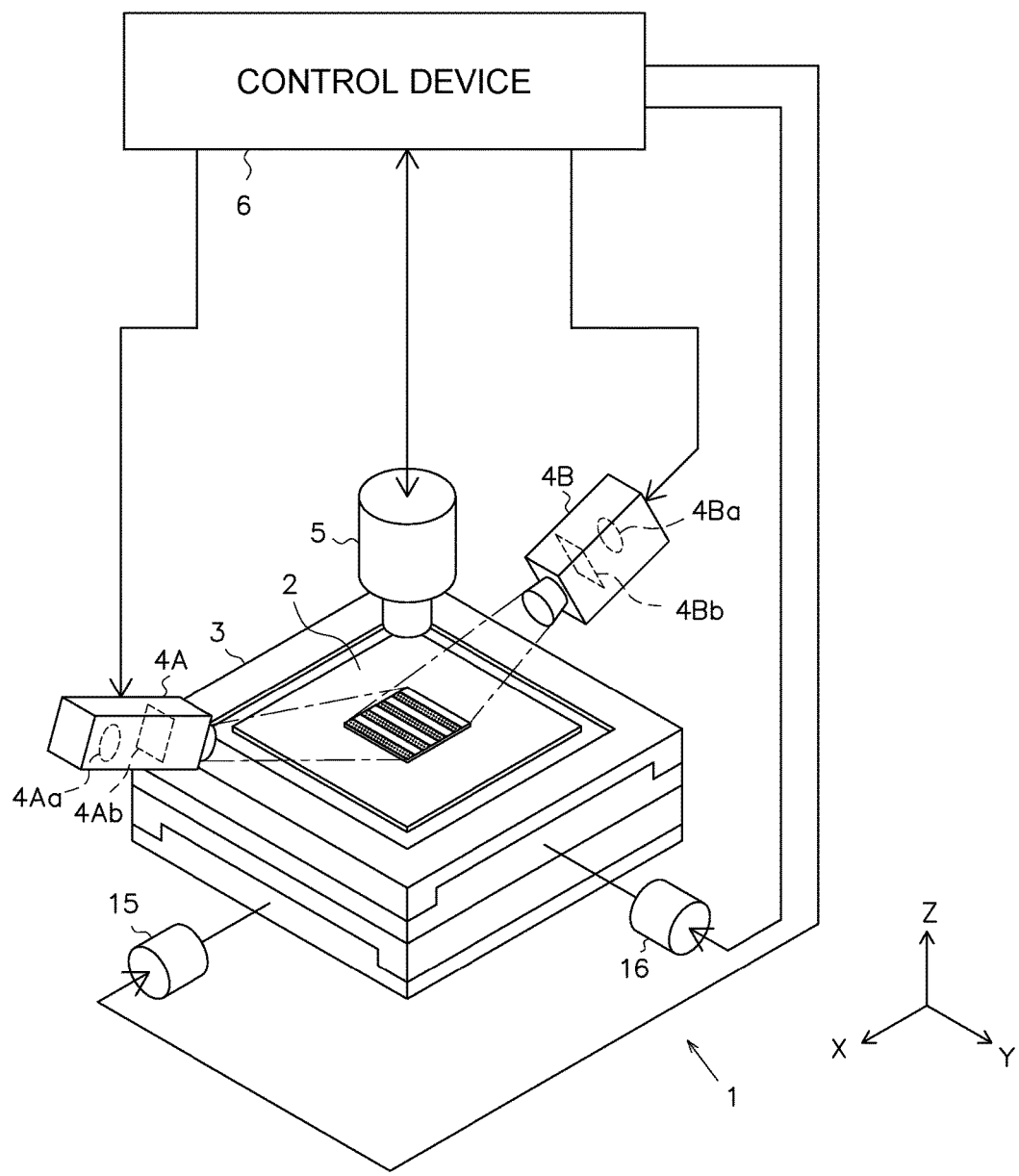
FIG. 1 is a schematic perspective view schematically illustrating a substrate inspection apparatus according to one or more embodiments of the invention.

The following describes one embodiment with reference to the drawings. FIG. 1 is a schematic configuration diagram schematically illustrating a substrate inspection apparatus 1 equipped with a three-dimensional measurement device according to this embodiment. As shown in FIG. 1, the substrate inspection apparatus 1 includes a mounting table 3 configured such that a printed circuit board 2 with solder paste as a measurement object printed thereon is placed on the mounting table 3, two illumination devices (a first illumination device 4A as a first irradiator and second illumination device 4B as a second irradiator) configured to irradiate the surface of the printed circuit board 2 obliquely downward with predetermined light patterns, a camera 5 as an imaging unit configured to take images of irradiated parts that are irradiated with the light patterns on the printed circuit board 2 and a control device 6 configured to perform various controls, image processing and arithmetic processing in the substrate inspection apparatus 1.

The mounting table 3 is provided with motors 15 and 16. The motors 15 and 16 are driven and controlled by the control device 6 to slide the printed circuit board 2 placed on the mounting table 3 in an arbitrary direction (X-axis direction and Y-axis direction).

The first illumination device 4A includes a first light source 4Aa configured to emit a predetermined light, and a first liquid crystal grid 4Ab that forms a first grid configured to convert the light from the first light source 4Aa into a first light pattern having a sinusoidal (striped) light intensity distribution. The first illumination device 4A is configured to irradiate the printed circuit board 2 obliquely downward with the striped first light pattern having a phase changing in multiple different ways (by every ¼ pitch according to this embodiment). A mechanism configured to control changeover of the grid configuration of the first liquid crystal grid 4Ab corresponds to the first grid controller.

Similarly, the second illumination device 4B includes a second light source 4Ba configured to emit a predetermined light, and a second liquid crystal grid 4Bb that forms a second grid configured to convert the light from the second light source 4Ba into a second light pattern having a sinusoidal (striped) light intensity distribution. The second illumination device 4B is configured to irradiate the printed circuit board 2 obliquely downward with the striped second light pattern having a phase changing in multiple different ways (by every ½ pitch according to this embodiment). A mechanism configured to control changeover of the grid configuration of the second liquid crystal grid 4Bb corresponds to the second grid controller.

More specifically, in each of the illumination devices 4A and 4B, the light emitted from the light source 4Aa or 4Ba is guided by an optical fiber into a pair of condenser lenses to be converted to parallel lights. The parallel lights are guided into a projection lens via the liquid crystal grid 4Ab or 4Bb. The striped light pattern is then radiated from the projection lens toward the printed circuit board 2.

Each of the liquid crystal grids 4Ab and 4Bb includes a liquid crystal layer that is formed between a pair of transparent substrates, a common electrode placed on one of the transparent substrate and a plurality of strip electrodes placed on the other transparent substrate to be opposed to the common electrode. A drive circuit controls on and off switching elements (for example, thin film transistors) respectively connected with the respective strip electrodes and regulates voltages that are to be applied to the respective strip electrodes, so as to change over the light transmittances of respective grid lines provided corresponding to the respective strip electrodes and thereby form a striped grid pattern including "bright portions" of the higher light transmittance and "dark portions" of the lower light transmittance. The light radiated onto the printed circuit board 2 via the liquid crystal grid 4Ab or 4Bb forms a light pattern having a sinusoidal light intensity distribution, due to a blur or the like caused by diffraction effect.

According to the embodiment, each of the illumination devices 4A and 4B is set to radiate each light pattern along the X-axis direction to be parallel to one pair of sides of the rectangular printed circuit board 2. Accordingly, the light pattern is radiated such that the stripes of the light pattern are perpendicular to the X-axis direction and are parallel to the Y-axis direction.

The respective illumination devices 4A and 4B are placed at positions opposed to each other across the printed circuit board 2 in the plan view (X-Y plane) along the approximate vertical direction (Z-axis direction) that is the imaging direction of the camera 5. The position where the first illumination device 4A is placed corresponds to the first position according to the embodiment, and the position where the second illumination device 4B is placed corresponds to the second position.

The camera 5 is configured to include a lens, an imaging element and the like. A CMOS sensor is employed for the imaging element. The imaging element is, however, not limited to the CMOS sensor but may be, for example, a CCD sensor or the like. Image data taken by the camera 5 are converted into digital signals inside of the camera 5, are input in the form of digital signals into the control device 6 and are stored in an image data storage device 24 described later. The control device 6 performs, for example, image processing and an inspection process as described later, based on the image data. From this point of view, the control device 6 is configured as the image processor according to the embodiment.

Figure 2:
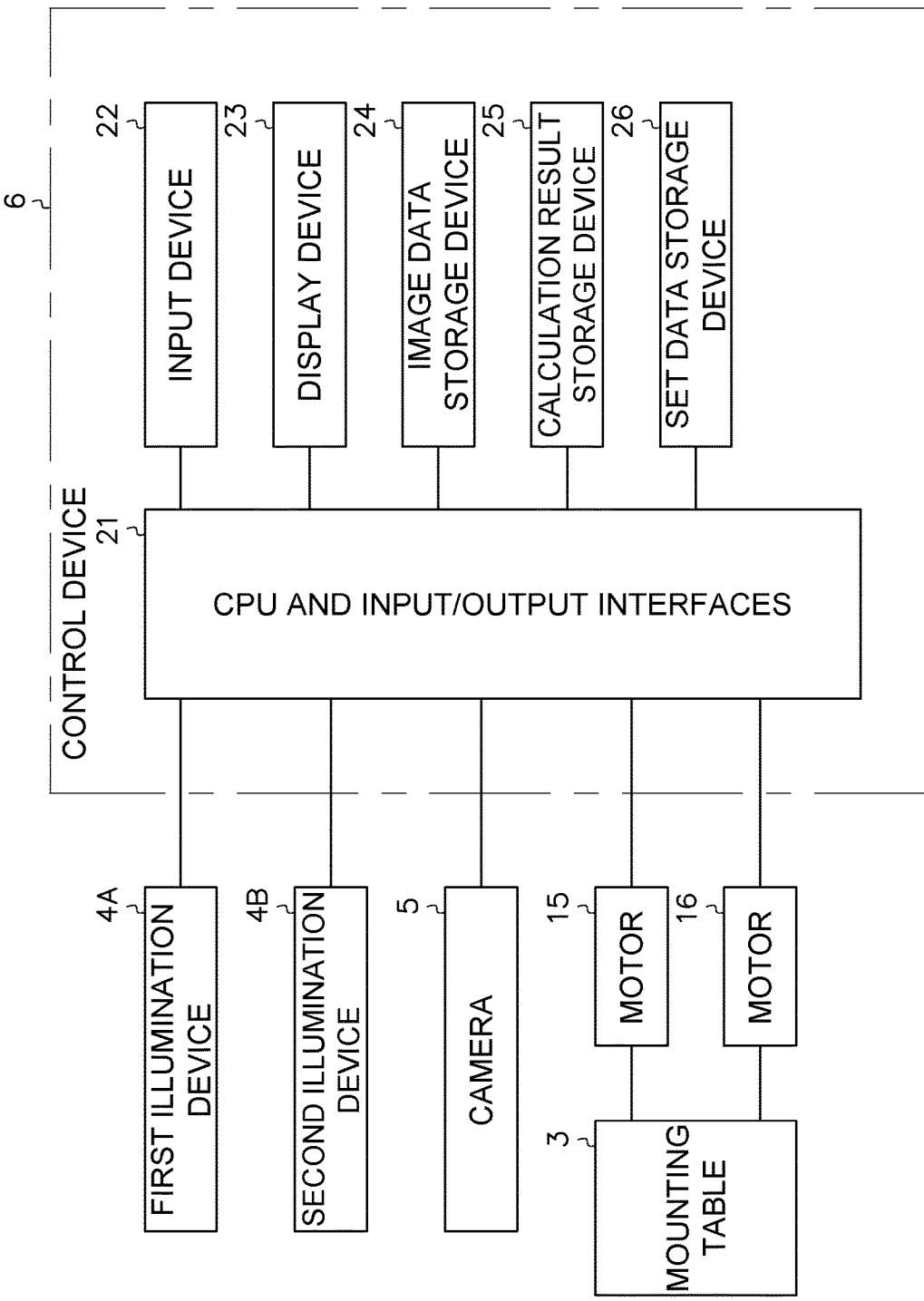
FIG. 2 is a block diagram illustrating the electrical configuration of the substrate inspection apparatus according to one or more embodiments of the invention.

The following describes the electrical configuration of the control device 6. As shown in FIG. 2, the control device 6 includes a CPU and input/output interfaces 21 (hereinafter referred to as "CPU and the like 21") configured to control the entire substrate inspection apparatus 1, an input device 22 configured by a keyboard and a mouse or by a touch panel as the "input unit", a display device 23 configured as the "display unit" including a display screen such as a CRT or a liquid crystal screen, an image data storage device 24 configured to store image data taken by the camera 5, a calculation result storage device 25 or memory configured to store various calculation results, and a set data storage device 26 configured to store various information in advance. These devices 22 to 26 are electrically connected with the CPU and the like 21.

The following describes an inspection procedure of the printed circuit board 2 by the substrate inspection apparatus 1 in detail. The procedure first performs calibration to check a variation (phase distribution) of the light pattern.

In the liquid crystal grids 4Ab and 4Bb, the voltage applied to each of the strip electrodes has a variation, due to variations in the characteristics (for example, offsets and gains) of the respective transistors connected with the respective strip electrodes. In the "bright portions" or "dark portions", the respective lines corresponding to the respective strip electrodes accordingly have variations in the light transmittance (luminance level). As a result, the light pattern radiated onto the measurement object is unlikely to have an ideal sinusoidal light intensity distribution and is thus likely to provide an error in the result of three-dimensional measurement.

Accordingly, calibration or the like is performed to check the variation (phase distribution) of the light pattern in advance.

The procedure of calibration first provides a reference surface that has a height position of 0 and forms a plane, separately from the printed circuit board 2. The reference surface has a color identical with the color of solder paste as the measurement object. Accordingly, the solder paste and the light pattern have equal reflectances.

The procedure subsequently irradiates the above reference surface with the light pattern and takes an image of the irradiated reference surface with the camera 5, so as to obtain image data including luminance values of the respective coordinates. According to this embodiment, in the calibration, the phase of the light pattern is shifted by 90 degrees each, and four different image data taken under each light pattern are obtained.

The control device 6 then calculates a phase $\theta$ of the light pattern in each pixel (coordinates) from the above four different image data and stores the calculated phases $\theta$ as calibration data in the set data storage device 26.

Additionally, the procedure of the embodiment specifies a gain A and an offset B of the light pattern in each pixel from the above four different image data with regard to the second liquid crystal grid 4Bb and a relationship between the gain A and the offset B, and stores the specified gains A, offsets B and their relationship as calibration data in the set data storage device 26. Accordingly, the set data storage device 26 is configured as the storage device according to the embodiment.

The following describes the procedure of calculating the gain A and the offset B more in detail. Relationships of the gain A and the offset B to luminance values ($V_0$, $V_1$, $V_2$, $V_3$) in each pixel of the four different image data are expressed by Expressions (H1), (H2), (H3) and (H4) given below:

[Math. 11]

$$V_0 = A \sin \theta + B \tag{H1}$$

$$V_1 = A \sin(\theta + 90°) + B = A \cos \theta + B \tag{H2}$$

$$V_2 = A \sin(\theta + 180°) + B = -A \sin \theta + B \tag{H3}$$

$$V_3 = A \sin(\theta + 270°) + B = -A \cos \theta + B \tag{H4}$$

Expression (H5) given below is derived by summing up the luminance values ($V_0$, $V_1$, $V_2$, $V_3$) of the four different image data and reorganizing Expressions (H1), (H2), (H3) and (H4) given above as shown in [Math. 12] given below:

[Math. 12]

$$\begin{aligned} V_0 + V_1 + V_2 + V_3 &= (A\sin\theta + B) + \\ &\quad (A\cos\theta + B) + (-A\sin\theta + B) + (-A\cos\theta + B) = 4B \\ B &= (V_0 + V_1 + V_2 + V_3)/4 \end{aligned} \tag{H5}$$

Expression (H6) given below is derived from Expressions (H1) and (H3) given above:

[Math. 13]

from $V_0 - V_2 = 2A \sin \theta$, $$\sin \theta = (V_0 - V_2)/2A \tag{H6}$$

Expression (H7) given below is derived from Expressions (H2) and (H4) given above:

[Math. 14]

from $V_1 - V_3 = 2A \cos \theta$, $$\cos \theta = (V_1 - V_3)/2A \tag{H7}$$

Expression (H9) given below is derived by substituting Expressions (H6) and (H7) given above into Expression (H8) given below and reorganizing these expressions as shown in [Math. 15] given below:

[Math. 15]

$$1 = \sin^2\theta + \cos^2\theta \quad (H8)$$
$$1 = \{(V_0 - V_2)/2A\}^2 + \{(V_1 - V_3)/2A\}^2$$
$$4A^2 = (V_0 - V_2)^2 + (V_1 - V_3)^2$$

$$A = \sqrt{\frac{(V_0 - V_2)^2 + (V_1 - V_3)^2}{4}} \quad (H9)$$

where $A > 0$

The proportional constant K of the gain A and the offset B is calculated according to Expression (H10) given below as being derived from Expressions (H5) and (H9) given above:

[Math. 16]

$$K = A/B \quad (H10)$$
$$= \frac{\sqrt{\frac{(V_0 - V_2)^2 + (V_1 - V_3)^2}{4}}}{\frac{V_0 + V_1 + V_2 + V_3}{4}}$$
$$= 2 \times \frac{\sqrt{(V_0 - V_2)^2 + (V_1 - V_3)^2}}{V_0 + V_1 + V_2 + V_3}$$

The gain A, the offset B and the proportional constant K of the light pattern in each pixel calculated as described above are stored as the calibration data in the set data storage device 26. A modified configuration may store only the proportional constant K as the calibration data.

Figure 3:
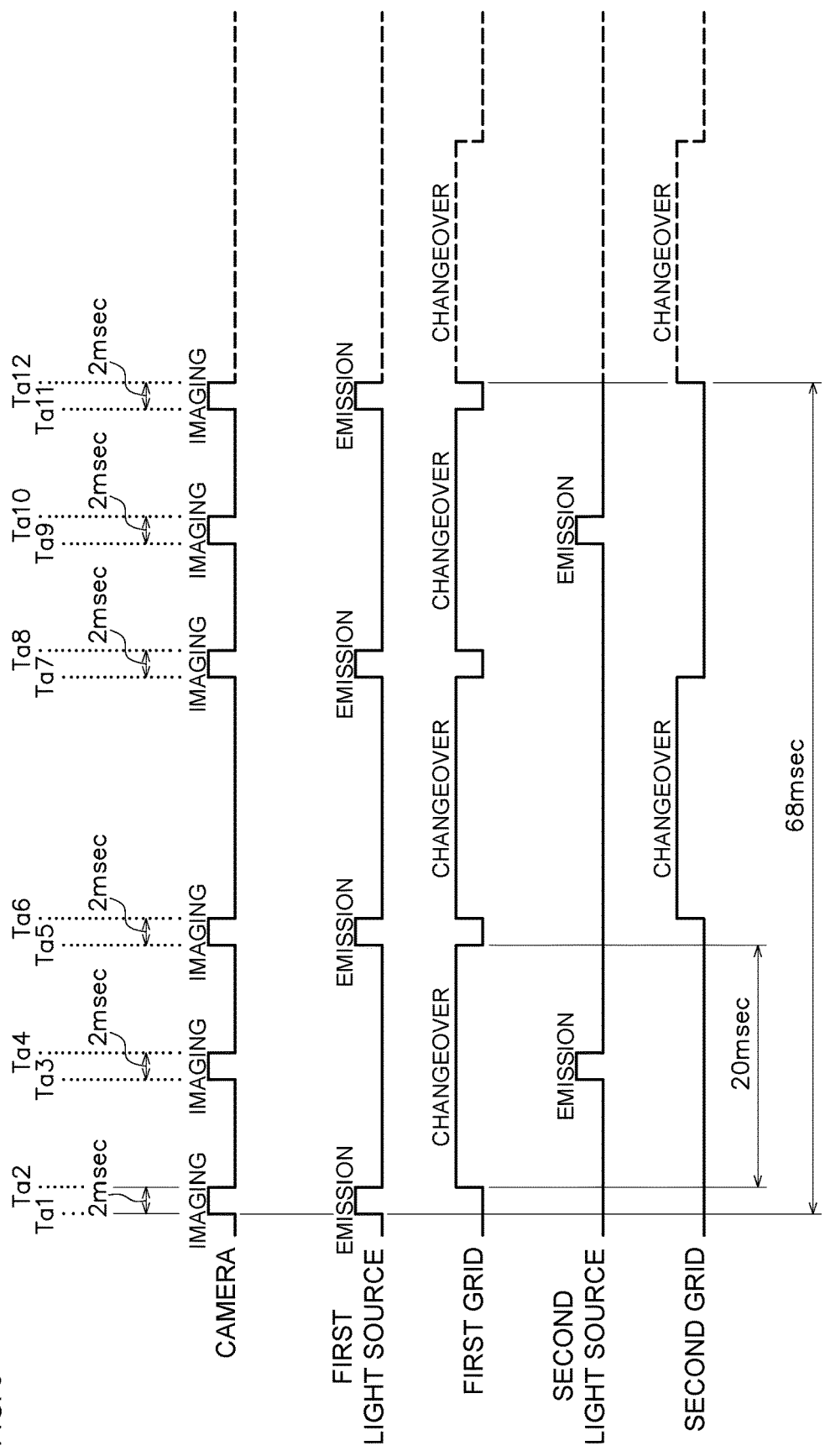
FIG. 3 is a timing chart showing processing operations of a camera and illumination devices according to one or more embodiments of the invention.
Figure 4:
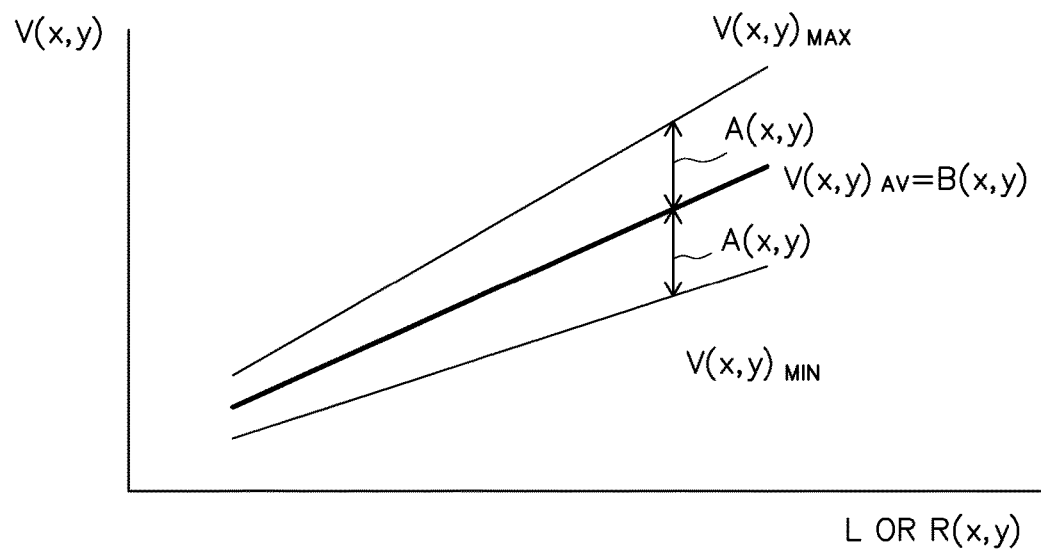
FIG. 4 is a graph showing a relationship between brightness or reflectivity of a light source and luminance value according to one or more embodiments of the invention.
Figure 5:
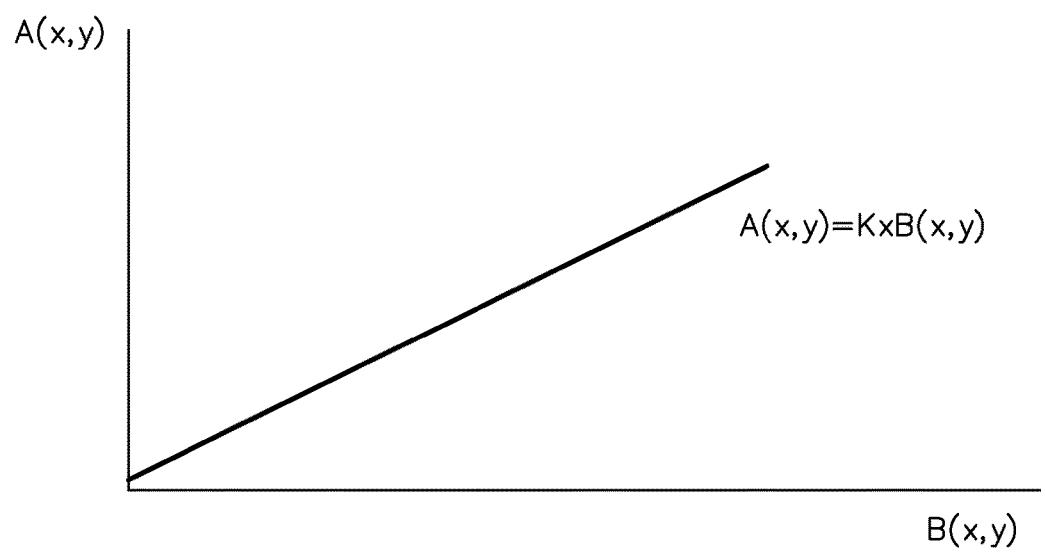
FIG. 5 is a graph showing a relationship between gain and offset according to one or more embodiments of the invention.

The following describes an inspection routine performed in each inspection area in detail with referring to the timing charge of FIG. 3. This inspection routine is performed by the control device 6 (CPU and the like 21).

The control device 6 first drives and controls the motors 15 and 16 to move the printed circuit board 2 and adjust the field of view of the camera 5 to a predetermined inspection area (measurement object area) on the printed circuit board 2. The inspection area denotes one of divisional areas provided by dividing the surface of the printed circuit board 2 in advance with setting the size of the field of view of the camera 5 as one unit.

The control device 6 subsequently performs changeover control of the liquid crystal grids 4Ab and 4Bb of both the illumination devices 4A and 4B and sets the positions of the first grid and the second grid formed in the respective liquid crystal grids 4Ab and 4Bb to predetermined reference positions (positions with the phase of "0 degree").

On completion of the changeover setting of the liquid crystal grids 4Ab and 4Bb, the control device 6 starts a first time of a first imaging process under the first light pattern with the phase of "0 degree" at a predetermined timing Ta1. More specifically, the control device 6 starts radiation of the first light pattern by emission of light from the first light source 4Aa of the first illumination device 4A and drives and controls the camera 5 to start imaging of an inspection area part irradiated with the first light pattern. This procedure of the first imaging process is similarly applied to second to fourth times of the first imaging process described later.

The control device 6 terminates the first time of the first imaging process at a timing Ta2 after elapse of a predetermined time period (2 msec according to the embodiment) since the start of imaging. More specifically, the control device 6 terminates radiation of the first light pattern and terminates the first time of imaging process with the first light pattern. The image data taken by the camera 5 are transferred to and stored in the image data storage device 24 (the same applies hereafter).

Simultaneously, the control device 6 starts a changeover process of the first liquid crystal grid 4Ab of the first illumination device 4A at the timing Ta2. More specifically, the control device 6 starts a process of changing the position of the first grid formed in the first liquid crystal grid 4Ab from the reference position (position with the phase of "0 degree") to a position with the phase of "90 degrees" where the phase of the first light pattern is shifted by ¼ pitch.

The control device 6 subsequently starts a first time of a second imaging process under the second light pattern with the phase of "0 degree" at a timing Ta3 in the middle of the changeover of the first liquid crystal grid 4Ab. More specifically, the control device 6 starts radiation of the second light pattern by emission of light from the second light source 4Ba of the second illumination device 4B and drives and controls the camera 5 to start imaging of an inspection area part irradiated with the second light pattern. This procedure of the second imaging process is similarly applied to a second time of the second imaging process described later.

The control device 6 terminates the first time of the second imaging process at a timing Ta4 after elapse of a predetermined time period (2 msec according to the embodiment) since the start of imaging. More specifically, the control device 6 terminates radiation of the second light pattern and terminates the first time of imaging process with the second light pattern.

The control device 6 then terminates the changeover process of the first liquid crystal grid 4Ab at a timing Ta5 after elapse of a predetermined time period (20 msec according to the embodiment) since the start of the changeover process (timing Ta2).

Simultaneously with completion of the changeover process of the first liquid crystal grid 4Ab, the control device 6 starts a second time of the first imaging process under the first light pattern with the phase of "90 degrees" at the timing Ta5, and terminates the second time of the first imaging process at a timing Ta6 after elapse of a predetermined time period (2 msec according to the embodiment) since the start of imaging.

Simultaneously with termination of the second time of the first imaging process, the control device 6 starts changeover processes of the liquid crystal grids 4Ab and 4Bb of both the illumination devices 4A and 4B at the timing Ta6. More specifically, the control device 6 starts a process of changing the position of the first grid formed in the first liquid crystal grid 4Ab of the first illumination device 4A from the position with the phase of "90 degrees" to a position with the phase of "180 degrees" where the phase of the first light pattern is shifted by ¼ pitch. The control device 6 also starts a process of changing the position of the second grid formed in the second liquid crystal grid 4Bb of the second illumination device 4B from the reference position (position with the phase of "0 degree") to a position with the phase of "180 degrees" where the phase of the second light pattern is shifted by ½ pitch.

Simultaneously with completion of the changeover process of the liquid crystal grids 4Ab and 4Bb, the control device 6 starts a third time of the first imaging process under the first light pattern with the phase of "180 degrees" at a timing Ta7, and terminates the third time of the first imaging process at a timing Ta8 after elapse of a predetermined time period (2 msec according to the embodiment) since the start of imaging.

Simultaneously, the control device 6 starts a changeover process of the first liquid crystal grid 4Ab of the first illumination device 4A at the timing Ta8. More specifically, the control device 6 starts a process of changing the position of the first grid formed in the first liquid crystal grid 4Ab from the position with the phase of "180 degrees" to a position with the phase of "270 degrees" where the phase of the first light pattern is shifted by ¼ pitch.

The control device 6 subsequently starts a second time of the second imaging process under the second light pattern with the phase of "180 degree" at a timing Ta9 in the middle of the changeover of the first liquid crystal grid 4Ab. The control device 6 terminates the second time of the second imaging process at a timing Ta10 after elapse of a predetermined time period (2 msec according to the embodiment) since the start of imaging.

The control device 6 then terminates the changeover process of the first liquid crystal grid 4Ab at a timing Ta11 after elapse of a predetermined time period (20 msec according to the embodiment) since the start of the changeover process (timing Ta8).

Simultaneously with completion of the changeover process of the first liquid crystal grid 4Ab, the control device 6 starts a fourth time of the first imaging process under the first light pattern with the phase of "270 degrees" at the timing Ta12, and terminates the fourth time of the first imaging process at a timing Ta11 after elapse of a predetermined time period (2 msec according to the embodiment) since the start of imaging.

The series of imaging processes described above obtains a total of six image planes of image data, i.e., four image planes of image data taken under the first light pattern with the four different phases and two image planes of image data taken under the second light pattern with the two different phases.

The control device 6 subsequently performs a first measurement process that performs height measurement (three-dimensional measurement) by the phase shift method, based on the four different image data obtained under the first light pattern. The function performing this first measurement process is configured as the first measurement unit according to the embodiment.

More specifically, the control device 6 calculates a phase θ1 of the first light pattern with regard to each pixel from the above four different image data (luminance values of each pixel) by the phase shift method.

Luminance values $V_{10}$, $V_{11}$, $V_{12}$ and $V_{13}$ of the above four different image data with regard to each pixel are expressed by Expressions (H1'), (H2'), (H3') and (H4') given below:

[Math. 17]

$$V_{10} = A \sin \theta_1 + B \quad \text{(H1')}$$

$$V_{11} = A \sin(\theta_1 + 90°) + B = A \cos \theta_1 + B \quad \text{(H2')}$$

$$V_{12} = A \sin(\theta_1 + 180°) + B = -A \sin \theta_1 + B \quad \text{(H3')}$$

$$V_{13} = A \sin(\theta_1 + 270°) + B = -A \cos \theta_1 + B \quad \text{(H4')}$$

where A denotes a gain and B denotes an offset.

Expression (H11) given below is derived by solving Expressions (H1'), (H2'), (H3') and (H4') given above with respect to the phase $\theta_1$:

[Math. 18]

$$\theta_{11} = \tan^{-1}\{(V_{10} - V_{12})/(V_{11} - V_{13})\} \quad \text{(H11)}$$

The control device 6 subsequently compares the phase $\theta_1$ of each pixel calculated as described above with the calibration data (the phase of each pixel based on calibration) stored in the set data storage device 26 described above to calculate a deviation amount in the pixel having the same phase, calculates height data (z) with regard to each pixel (x,y) in the inspection area based on the principle of triangulation, and stores the calculated height data (z) into the calculation result storage device 25.

For example, when an observed value (phase) in a measurement object pixel (x,y) is "10 degrees", the control device 6 detects the position of the value "10 degrees" on the data stored by calibration. When the value "10 degrees" is present at a pixel three pixels away from the measurement object pixel (x,y), this means that the stripe of the light pattern is deviated by three pixels. The height data (z) of the measurement object pixel (x,y) may be determined by the principle of triangulation, based on the radiation angle of the light pattern and the deviation amount of the stripe of the light pattern.

The measurement data obtained by the above first measurement process, however, has deficiency of data with regard to a region (pixels) that is not sufficiently irradiated with the first light pattern and has difficulty in measurement by the first measurement process.

The control device 6 subsequently performs a process of complementing the above deficiency of data. More specifically, the control device 6 first identifies a region (portion having deficiency of data) that has difficulty in measurement by the first measurement process, based on the measurement result of the above first measurement process. The control device 6 subsequently performs a second measurement process that performs height measurement (three-dimensional measurement) by the phase shift method, based on the above two different image data obtained under the second light pattern, with regard to the identified region. The function performing the second measurement process is configured by the second measurement unit according to the embodiment.

More specifically, the control device 6 calculates a phase $\theta_2$ of the second light pattern with regard to each pixel by the phase shift method, based on the above two different image data (luminance values of each pixel) and the calibration data (proportional constant K of each pixel based on calibration) stored in the set data storage device 26.

When the above two different image data have luminance values $V_{20}$ and $V_{21}$ with regard to each pixel, the phase $\theta_2$ of the second light pattern with regard to each pixel is expressed by Expression (H12) given below, based on Expression (15) given above:

$$\theta_2 = \sin^{-1}[(V_{20} - V_{21})/K(V_{20} + V_{21})] \quad \text{(H12)}$$

where K denotes a proportional constant.

Like the first measurement process described above, the control device 6 subsequently compares the phase $\theta_2$ of each pixel calculated as described above with the calibration data (the phase of each pixel based on calibration) stored in the set data storage device 26 described above to calculate a deviation amount in the pixel having the same phase, calculates height data (z) with regard to each pixel (x,y) in the inspection area based on the principle of triangulation, and stores the calculated height data (z) into the calculation result storage device 25.

After termination of the above second measurement process, the control device 6 performs a combining process to combine the measurement data (measurement value) obtained by the first measurement process with measurement data (measurement value) obtained by the second measurement process. This completes measurement data without deficiency with regard to respective pixels in an entire predetermined inspection area with complementation of the deficiency of data in the measurement data obtained by the first measurement process. The combining process is configured as the measurement value acquirer according to the embodiment.

The control device 6 subsequently detects a printing area of solder paste that is higher than the reference surface, based on the measurement data of the predetermined inspection area thus obtained, integrates the height of each site in this area and calculates the printed volume of solder paste.

The control device 6 then compares the data such as the position, the area, the height or the volume of the solder paste thus obtained with reference data stored in advance in the set data storage device 26, and determines the good/poor quality of the printing state of solder paste in the inspection area, based on whether the result of comparison is in an allowable range.

During this process, the control device 6 drives and controls the motors 15 and 16 to move the printed circuit board 2 to a next inspection area. The above series of process is then repeatedly performed with regard to all the inspection areas, so that inspection of the entire printed circuit board 2 is completed.

As described above in detail, the configuration of the embodiment radiates the light patterns from two different directions and thereby suppresses generation of any shadow part of the printed circuit board 2 that is not irradiated with the light pattern. The configuration of the embodiment using the two light patterns obtains the measurement result of the first measurement process with the high measurement accuracy using the first light pattern with regard to a region that is measurable by radiation of the first light pattern, as the measurement value of this region, while obtaining the measurement result of the second measurement process using the second light pattern with regard to a region that has difficulty in measurement by radiation of the first light pattern, as the measurement value of this region. The configuration of the embodiment accordingly obtains measurement data having the high measurement accuracy and no deficiency of data as a whole. As a result, this enhances the measurement accuracy.

According to the embodiment, measurement based on radiation of the second light pattern uses the relationship between the gain A and the offset B [for example, A=K (proportional constant)×B] determined according to a predetermined imaging condition and the value of a gain A(x,y) or an offset B(x,y) with regard to each pixel (x,y) determined from a luminance value V(x,y) of the pixel (x,y) on the image data. This allows for height measurement by the phase shift method, based on the two different image data taken under the light pattern with two different phases.

Accordingly, the embodiment performs four first imaging processes under the first light pattern with four different phases and two second imaging processes under the second light pattern with two different phases. This requires a total of six imaging processes. This reduces the total number of imaging processes and shortens the imaging time, compared with the prior art that requires a total of eight imaging processes, i.e., four processes with regard to each light pattern. As a result, this enables measurement of the higher accuracy to be performed in a shorter time period.

Additionally, the configuration of the embodiment enables one cycle of the second imaging process under the second light pattern to be performed in the middle of the changeover process of the first liquid crystal grid 4Ab of the first illumination device 4A, after performing one cycle of the first imaging process under the first light pattern.

This configuration shortens the time period required for completion of all imaging processes (last imaging process) with regard to a predetermined inspection area. For example, according to this embodiment, the time period required for completion of all the imaging processes with regard to the predetermined inspection area is [time period required for the first imaging process [2 ms]×4 times]+[time period required for the changeover process of the first liquid crystal grid 4Ab [20 ms]×3 times]=total of [68 msec].

Furthermore, according to this embodiment, the printed circuit board 2 is at stop during at least acquisition of data with regard to the predetermined inspection area (during the above series of imaging processes described above). This fixes the positional relationship of the printed circuit board to the camera 5. Since the positional relationship of the printed circuit board 2 to the camera 5 is not changed during imaging, this prevents the inspection area from being narrowed or the like. As a result, this shortens the measurement time in measurement of the printed circuit board 2 with a large number of inspection areas set thereon like this embodiment.

Second Embodiment

The following describes a second embodiment with reference to drawings. The like components to those of the first embodiment are expressed by the like reference signs, and their detailed description is omitted.

The above first embodiment is configured to determine in advance the relationship between the gain A and the offset B (proportional constant K) of the light pattern with regard to each pixel by calibration. Alternatively, the second embodiment is configured to determine the relationship between the gain A and the offset B (proportional constant K) of the second light pattern, based on two different image data actually taken under the second light pattern with two different phases.

Figures 6, 7:
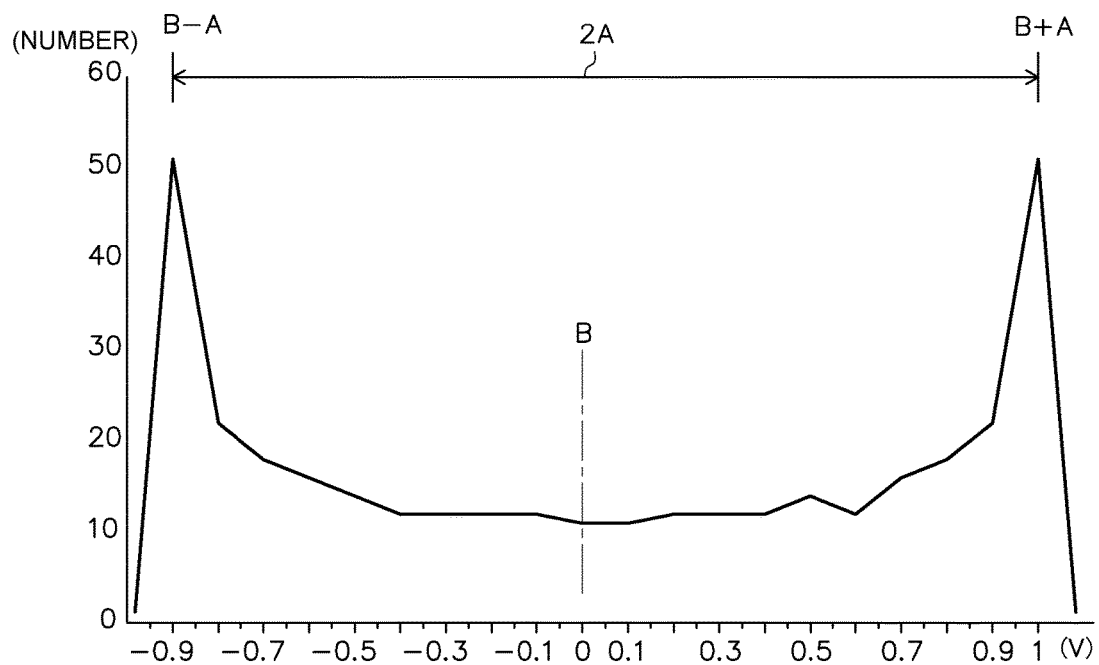
FIG. 6 is a distribution table showing a frequency distribution of luminance values included in respective data divisions according to one or more embodiments of the invention.
FIG. 7 is a histogram showing the frequency distribution of luminance values included in the respective data divisions according to one or more embodiments of the invention.

The procedure first determines the values of the offset B with regard to all the pixels of the image data according to Expression (12) given above. The procedure then extracts luminance values V(=A sin θ+B) of the pixels having an identical value of the offset B among them and creates a histogram of the extracted luminance values. One example is shown in the table of FIG. 6 and FIG. 7. FIGS. 6 and 7 show the case where the gain A is equal to "1" and the offset B is equal to "0". FIG. 6 is a distribution table showing the frequencies of luminance values included in respective data districts when the luminance values V are divided into data districts of a width "0.1", and FIG. 7 is a histogram obtained by plotting these frequencies.

A maximum value $V_{MAX}$ and a minimum value $V_{MIN}$ of the luminance value are then determined, based on this histogram. Two peaks appearing in the histogram may be determined respectively as the maximum value $V_{MAX}$ and the minimum value $V_{MIN}$ of the luminance value by utilizing the characteristic of "sin θ". In the example of FIGS. 6 and 7, the frequencies of the luminance values V in a data district of "−1.0 to −0.9" and in a data district of "0.9 to 1.0" are respectively "51", which form the two peaks.

A gain A and an offset B are subsequently calculated, based on the maximum value $V_{MAX}$ and the minimum value $V_{MIN}$ of the luminance value. As described above, the offset B is an average value of the maximum value $V_{MAX}$ and the minimum value $V_{MIN}$ of the luminance value, and the gain A is half the difference between the maximum value $V_{MAX}$ and the minimum value $V_{MIN}$. As shown in FIG. 7, the offset B is an intermediate value of the two peaks, and the gain A is half the width of the two peaks.

The proportional constant K may be determined based on the values of the gain A and the offset B obtained as described above [as shown by Expression (3) given above]. Accordingly, the above series of processing function to determine the proportional constant K is configured as the relationship grasping unit according to the embodiment.

This embodiment has similar functions and advantageous effects to those of the first embodiment. The configuration of this embodiment saves the labor of calibration that is performed in the above embodiment and further shortens the measurement time.

The configuration of this embodiment determines the proportional constant K and the like with regard to all the pixels of image data, based on the two different image data taken under the second light pattern having the two different phases by 180 degrees. This configuration is, however, not essential, but a modification may be configured to determine the proportional constant K and the like, based on two different image data taken under the second light pattern having two different phases by 90 degrees. Another modification may be configured to determine the proportional constant K and the like not with regard to all the pixels of image data but with regard to a range of part of image data, for example, the periphery of a measurement object data.

Third Embodiment

The following describes a third embodiment with reference to drawings. The like components to those of the first embodiment are expressed by the like reference signs, and their detailed description is omitted.

This embodiment differs from the first embodiment by an inspection routine that is performed in each inspection area. The inspection routine according to this embodiment is described in detail with reference to the timing chart of FIG. 8.

The control device 6 first drives and controls the motors 15 and 16 to move the printed circuit board 2 and adjust the field of view of the camera 5 to a predetermined inspection area (measurement object area) on the printed circuit board 2.

The control device 6 subsequently performs changeover control of the liquid crystal grids 4Ab and 4Bb of both the illumination devices 4A and 4B and sets the positions of the first grid and the second grid formed in the respective liquid crystal grids 4Ab and 4Bb to predetermined reference positions (positions with the phase of "0 degree").

On completion of the changeover setting of the liquid crystal grids 4Ab and 4Bb, the control device 6 starts a first time of a second imaging process under the second light pattern with the phase of "0 degree" at a predetermined timing Tb1, and terminates the first time of the second imaging process at a timing Tb2 after elapsed of a predetermined time period (2 msec according to the embodiment).

Simultaneously with termination of the second imaging process, the control device 6 starts a first time of a first imaging process under the first light pattern with the phase of "0 degree2 at the timing Tb2, and terminates the first time of the first imaging process at a timing Tb3 after elapse of a predetermined time period (2 msec according to the embodiment).

Simultaneously with termination of the first imaging process, the control device 6 starts changeover processes of the liquid crystal grids 4Ab and 4Bb of both the illumination devices 4A and 4B at the timing Tb3. More specifically, the control device 6 starts a process of changing the position of the first grid formed in the first liquid crystal grid 4Ab of the first illumination device 4A from the reference position (position with the phase of "0 degree") to a position with the phase of "90 degrees" where the phase of the first light pattern is shifted by ¼ pitch. The control device 6 also starts a process of changing the position of the second grid formed in the second liquid crystal grid 4Bb of the second illumination device 4B from the reference position (position with the phase of "0 degree") to a position with the phase of "180 degrees" where the phase of the second light pattern is shifted by ½ pitch.

The control device 6 then terminates the changeover processes of the liquid crystal grids 4Ab and 4Bb at a timing Tb4 after elapse of a predetermined time period (20 msec according to the embodiment) since the start of the changeover processes (timing Tb3).

Simultaneously with completion of the changeover processes of the liquid crystal grids 4Ab and 4Bb, the control device 6 starts a second time of the first imaging process under the first light pattern with the phase of "90 degrees" at the timing Tb4, and terminates the second time of the first imaging process at a timing Tb5 after elapse of a predetermined time period (2 msec according to the embodiment) since the start of imaging.

Simultaneously, the control device 6 starts a changeover process of the first liquid crystal grid 4Ab of the first illumination device 4A at the timing Tb5. More specifically, the control device 6 starts a process of changing the position of the first grid formed in the first liquid crystal grid 4Ab of the first illumination device 4A from the position with the phase of "90 degrees" to a position with the phase of "180 degrees" where the phase of the first light pattern is shifted by ¼ pitch.

The control device 6 then terminates the changeover process of the first liquid crystal grid 4Ab at a timing Tb6 after elapse of a predetermined time period (20 msec according to the embodiment) since the start of the changeover process (timing Tb5).

Simultaneously with completion of the changeover process of the first liquid crystal grid 4Ab, the control device 6 starts a third time of the first imaging process under the first light pattern with the phase of "180 degrees" at the timing Tb6, and terminates the third time of the first imaging process at a timing Tb7 after elapse of a predetermined time period (2 msec according to the embodiment) since the start of imaging.

Simultaneously, the control device 6 starts a changeover process of the first liquid crystal grid 4Ab of the first illumination device 4A at the timing Tb7. More specifically, the control device 6 starts a process of changing the position of the first grid formed in the first liquid crystal grid 4Ab of the first illumination device 4A from the position with the phase of "180 degrees" to a position with the phase of "270 degrees" where the phase of the first light pattern is shifted by ¼ pitch.

The control device 6 then terminates the changeover process of the first liquid crystal grid 4Ab at a timing Tb8 after elapse of a predetermined time period (20 msec according to the embodiment) since the start of the changeover process (timing Tb7).

Simultaneously with completion of the changeover process of the first liquid crystal grid 4Ab, the control device 6 starts a fourth time of the first imaging process under the first light pattern with the phase of "270 degrees" at the timing Tb8, and terminates the fourth time of the first imaging process at a timing Tb9 after elapse of a predetermined time period (2 msec according to the embodiment) since the start of imaging.

Simultaneously with termination of the first imaging process, the control device 6 starts a second time of the second imaging process under the second light pattern with the phase of "180 degrees" at the timing Tb9, and terminates the second time of the second imaging process at a timing Tb10 after elapse of a predetermined time period (2 msec according to the embodiment).

The series of imaging processes described above obtains a total of six image planes of image data, i.e., four image planes of image data taken under the first light pattern with the four different phases and two image planes of image data taken under the second light pattern with the two different phases.

As described above in detail, like the first embodiment, the configuration of this embodiment also shortens the time period required for completion of all imaging processes (last imaging process) with regard to a predetermined inspection area. For example, according to this embodiment, the time period required for completion of all the imaging processes with regard to the predetermined inspection area is [time period required for the first imaging process [2 ms]×4 times]+[time period required for the changeover process of the first liquid crystal grid 4Ab [20 ms]×3 times]+[time period required for the second imaging process [2 ms]×2 times]=total of [72 msec].

The present disclosure is not limited to the description of the above embodiments but may be implemented, for example, by configurations described below. The present disclosure may also be naturally implemented by applications and modifications other than those illustrated below.

(a) According to the above embodiments, the three-dimensional measurement device is embodied in the substrate inspection apparatus 1 configured to measure the height of solder paste printed and formed on the printed circuit board 2. This is, however, not restrictive. For example, the three-dimensional measurement device may be embodied in a configuration of measuring the height of another object, for example, a solder bump printed on a substrate or an electronic component mounted on a substrate.

(b) The above embodiment employs the liquid crystal grids 4Ab and 4Bb for the grids configured to convert the lights from the light sources 4Aa and 4Ba into striped light patterns and is configured to shift the phases of the light patterns by changeover control of the liquid crystal grids 4Ab and 4Bb. This configuration is, however, not restrictive. For example, a modification may be configured to move grid members by moving units such as piezoelectric actuators, so as to shift the phases of the light patterns.

(c) According to the above embodiment, the first measurement process is configured to perform three-dimensional measurement by the phase shift method, based on the four different image data taken under the first light pattern having the four different phases that differ by 90 degrees each. This configuration is, however, not restrictive. For example, a modification may be configured to perform three-dimensional measurement, based on three different image data taken under the first light pattern having three different phases that differ by 120 degrees each. Accordingly, the "predetermined first number" that denotes the number of imaging processes under the first light pattern may be any number that allows for at least three-dimensional measurement by the phase shift method.

(d) According to the above embodiment, the second measurement process is configured to perform three-dimensional measurement by the phase shift method, based on the two different image data taken under the light pattern having the two different phases that differ by 180 degrees. This configuration may be replaced by, for example, a modification configured to perform three-dimensional measurement, based on two different image data taken under a light pattern having two different phases that differ by 90 degrees. In this modification, the phase $\theta_2$ of the second light pattern in each pixel may be calculated from the luminance values $V_{20}$ and $V_{21}$ in each pixel of the two different image data and the known proportional constant K according to Expressions (23) and (27) given above.

This modified configuration determines the phase $\theta_2$ according to the arithmetic expression using "$\tan^{-1}$". This allows for measurement of the height in the range of 360 degrees from −180 degrees to 180 degrees and further expands the measurement range.

Any other configuration that satisfies the relations of Expressions (1), (2) and (3) given above may also be employed. An example of the general expression to obtain the phase $\theta_2$ is Expression (9) given above (as shown in [Math. 9]).

(e) According to the above embodiment, the second measurement process is configured to perform three-dimensional measurement, based on the two different image data taken under the light pattern with the two different phases. The "predetermined second number" that denotes the number of imaging processes under the second light pattern may be any number that is at least smaller than the "predetermined first number" that denotes the number of imaging processes under the first light pattern. For example, when the measurement with the first light pattern is configured to perform height measurement based on the four different image data taken under the first light pattern with the four different phases, the measurement with the second light pattern may be configured to perform height measurement using the relationship between the gain A and the offset B (proportional constant K), based on three different image data taken under the second light pattern with three different phases. This modified configuration also enables the phase $\theta_2$ of the second light pattern to be determined according to a relatively simple arithmetic expression compared with the conventional configuration and thereby achieves the higher speed processing.

(f) The above first embodiment is configured to perform calibration, based on the four different image data taken under the light pattern having the four different phases that differ by 90 degrees each. This is, however, not restrictive. For example, a modification may be configured to perform calibration, based on three different image data taken under the light pattern having three different phases.

Another modification may be configured to perform calibration a plurality of times with changing the luminance of the light source. This configuration enables a dark current (offset) C of the camera 5 to be determined according to Expression (28) given below:

$$A = KB + C \qquad (28)$$

where A denotes a gain, B denotes an offset, C denotes a dark current (offset) of the camera, and K denotes a proportional constant.

In place of the configuration that expresses the relationship between the gain A and the offset B by an expression, another modification may be configured to generate a numerical table or table data expressing the relationship between the gain A and the offset B and to determine the offset B from the gain A or determine the gain A from the offset B.

In place of the calibration, the relationship between the gain A and the offset B (proportional constant K) may be determined from the four different image data taken under the first light pattern with the four different phases used in the first measurement process. The function performing this process may be configured as the relationship grasping unit according to the embodiment.

Figure 8:
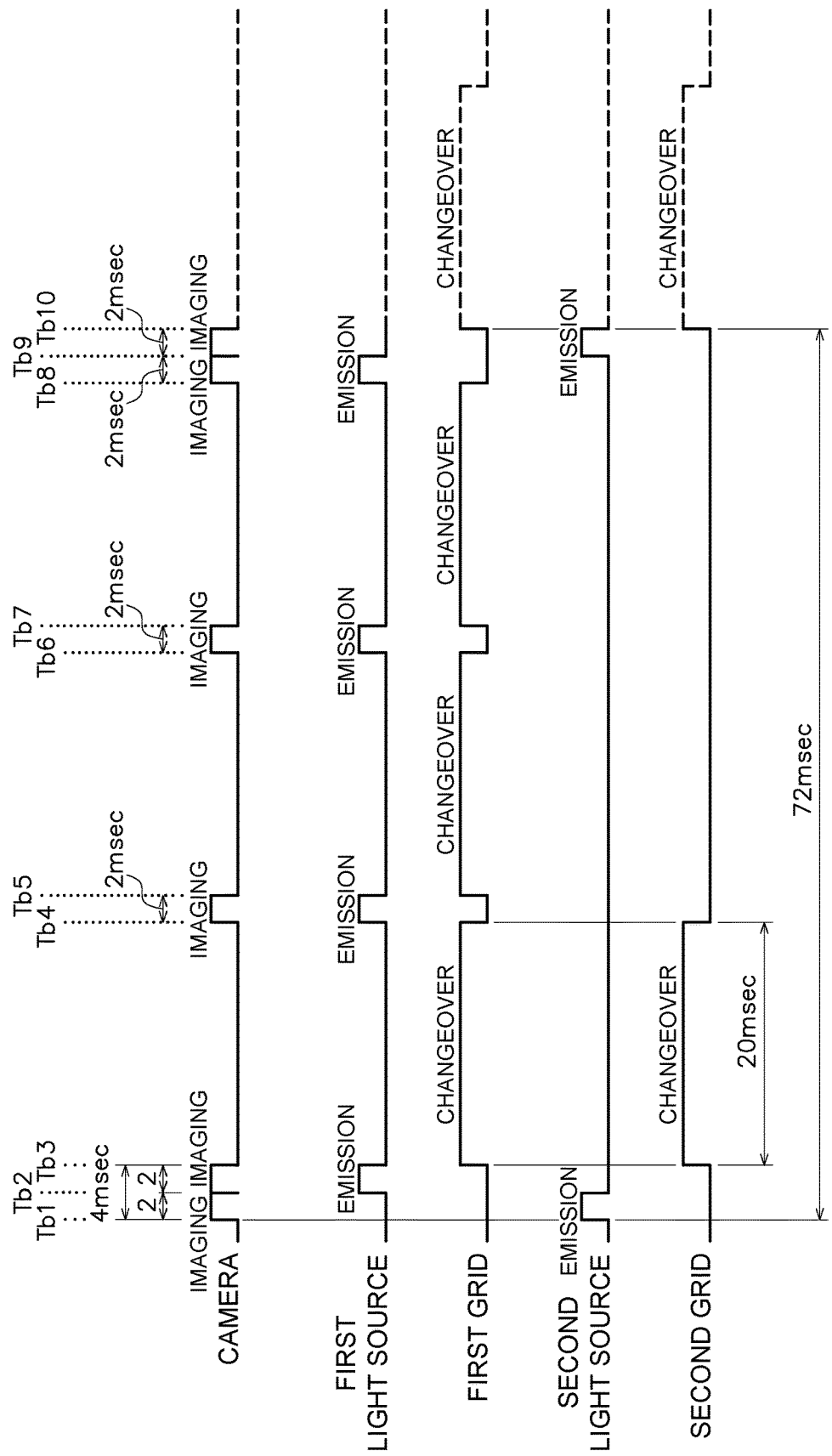
FIG. 8 is a timing chart showing processing operations of a camera and illumination devices according to one or more embodiments of the invention.

(g) For example, the sequence of performing the first imaging process and the second imaging process and the execution timings of the changeover processes of the liquid crystal grids 4Ab and 4Bb in the inspection routine are not limited to those of the above first embodiment (shown in FIG. 3) or to those of the above third embodiment (shown in FIG. 8). There may be various other combinations according to, for example, the number of the first imaging processes and the number of the second imaging processes.

For example, the above first embodiment is configured to start the changeover processes of both the liquid crystal grids 4Ab and 4Bb simultaneously after elapse of a predetermined time period (for example, after 11 msec) since termination of the first time of the second imaging process. This is, however, not restrictive. For example, a modification may be configured to start the changeover process of the second liquid crystal grid 4Bb alone simultaneously with termination of the second imaging process or after elapse of a predetermined time period (for example, after 4 msec) since termination of the second imaging process. In other words, the modification may be configured to perform the changeover process of the first liquid crystal grid 4Ab and the changeover process of the second liquid crystal grid 4Bb in a partly overlapping manner and to perform a second time of the first imaging process during the changeover process of the second liquid crystal grid 4Bb. In order to suppress a decrease in the measurement accuracy of the first measurement process, however, the changeover process of the second liquid crystal grid 4Bb may be performed simultaneously with the changeover process of the first liquid crystal grid 4Ab, like the above first embodiment.

(h) The above embodiment is configured to mainly use the measurement result of the first measurement process having the high measurement accuracy and complement the partial deficiency of data with the measurement result of the second measurement process, thus obtaining measurement data having high measurement accuracy and little deficiency of data as a whole. This is, however, not restrictive. A modification may be configured to mainly use the measurement result of the second measurement process and complement the partial deficiency of data with the measurement result of the first measurement process.

The above embodiment is configured to perform the second measurement process with regard to only the regions having difficulty in measurement by the first measurement process. This is, however, not restrictive. A modification may be configured to perform the second measurement process with regard to all regions in a predetermined inspection area that allow for three-dimensional measurement based on the two different image data taken under the second light pattern and extract data corresponding to the regions having difficulty in measurement by the first measurement process.

(i) In the description of the above embodiments, the imaging process of the camera 5 is simply expressed as "imaging". More specifically, the imaging process includes an exposure process as substantial imaging and a data transfer process of taken image data.

Figure 9A:
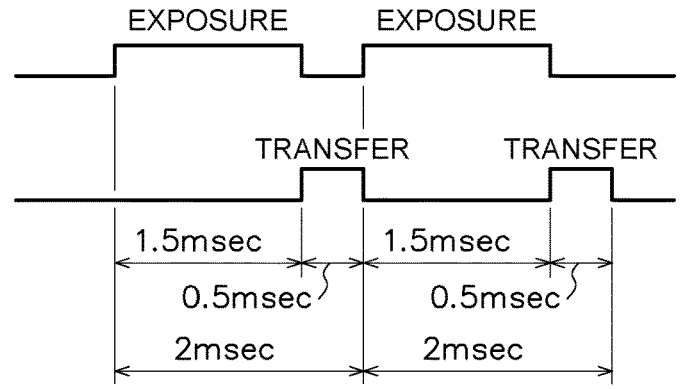
FIGS. 9A to 9C are timing charts showing processing operations with regard to exposure of the camera and data transfer according to one or more embodiments of the invention.

Accordingly, when a general CCD camera or the like is used as the camera 5, data transfer is not allowed during exposure. When the first imaging process and the second imaging process are performed successively like the above third embodiment, the exposure process and the data transfer process are repeated alternately as shown in an example of FIG. 9A.

When a CMOS camera or a CCD camera with the function that allows for exposure during data transfer is used as the camera 5, on the other hand, the exposure process and the data transfer process may be performed in a partly overlapping manner. This shortens the imaging time and thereby the measurement time.

Figure 9B:
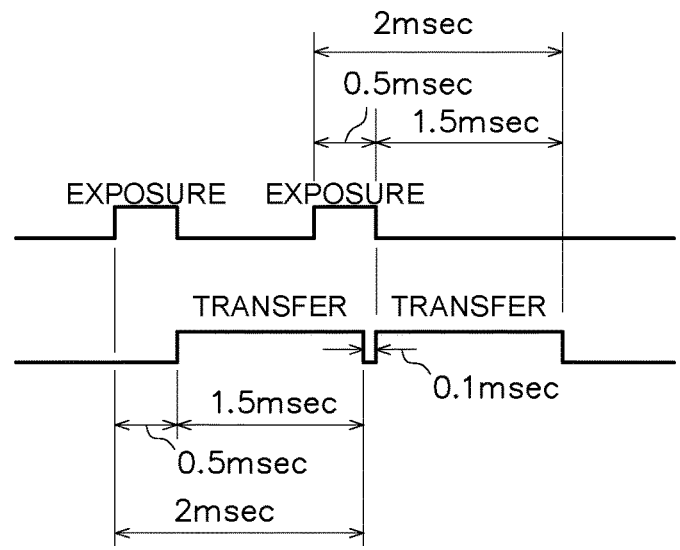

More specifically, when the exposure time is set to be shorter than the transfer time, as shown in an example of FIG. 9B, starting second exposure at the last moment such that the second exposure does not terminate during first data transfer obtained by first exposure minimizes the imaging time required for the first imaging process and the second imaging process, while preventing data obtained by the first exposure from being lost.

Figure 9C:
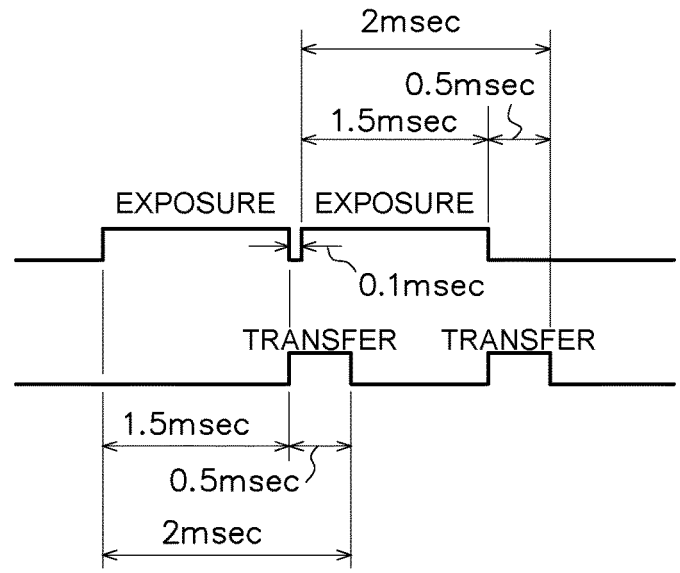
Figure 10:
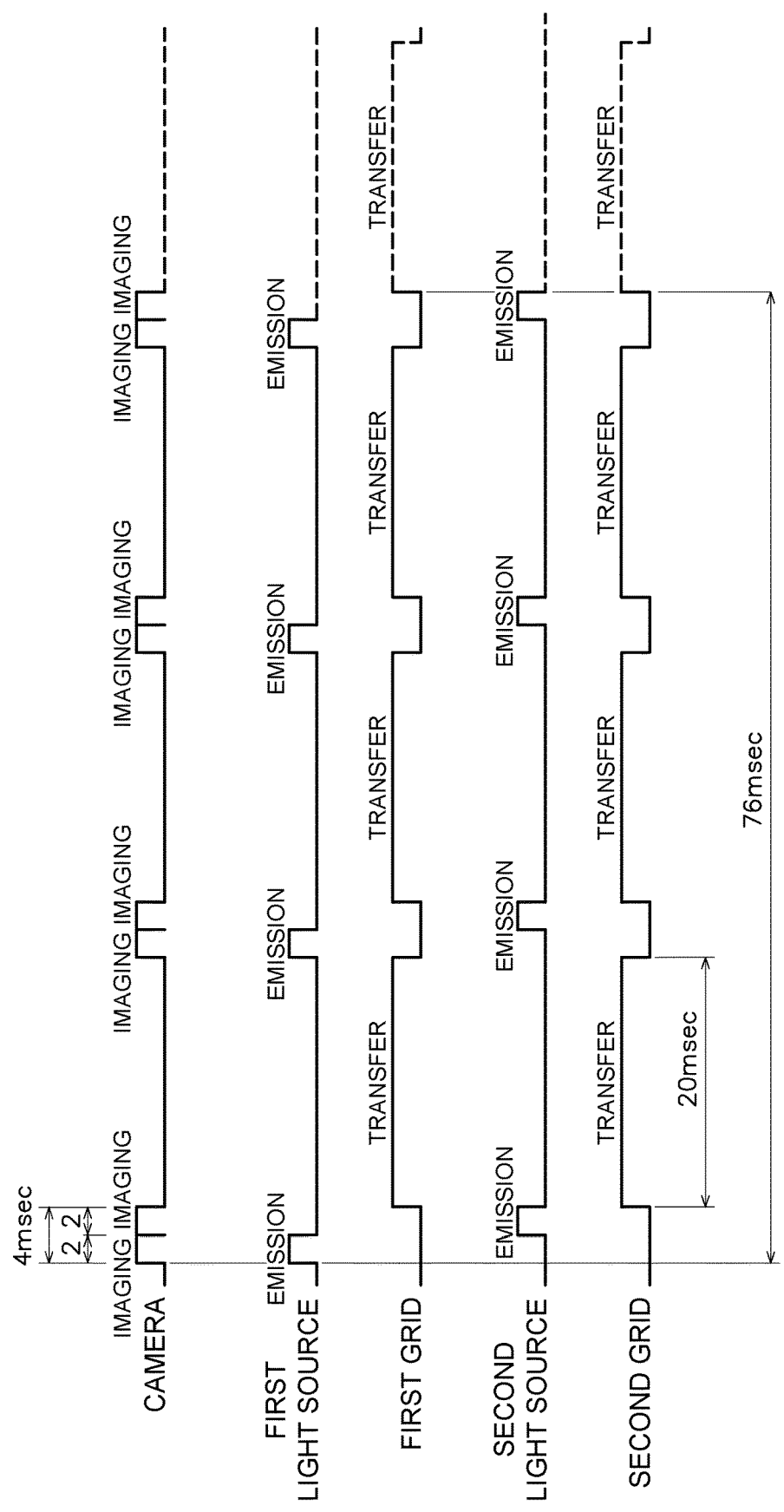
FIG. 10 is a timing chart showing processing operations of a conventional camera and conventional illumination devices according to one or more embodiments of the invention.

When the exposure time is set to be longer than the transfer time, on the other hand, as shown in an example of FIG. 9C, starting second exposure immediately after termination of first exposure minimizes the imaging time required for the first imaging process and the second imaging process.

(j) According to the above embodiment, the illumination devices 4A and 4B are placed at the positions opposed to each other across the printed circuit board 2 in the plan view (X-Y plane) viewed along the approximately vertical direction (Z-axis direction9 that is the imaging direction of the camera 5 and are arranged at equal intervals about the printed circuit board 2 in the plan view. This arrangement is, however, not restrictive. The arrangement of the illumination devices 4A and 4B may be set arbitrarily according to the configuration of the printed circuit board 2 or the like, in order not to generate any shadow part that is not irradiated with each light pattern.

For example, according to the above embodiment, the respective light patterns are radiated along the X-axis direction to be parallel to one pair of sides of the rectangular printed circuit board 2. Accordingly, the light pattern is radiated such that the stripes of the light pattern are perpendicular to the X-axis direction and are parallel to the Y-axis direction. This configuration is, however, not restrictive. For example, the light pattern may be radiated such that the stripes of the light pattern obliquely (for example, to be inclined at 45 degrees in the plan view) intersect with respective sides of the rectangular printed circuit board 2 and the imaging field (inspection area) of the camera 5.

(k) The above embodiments do not specifically refer to the periods (stripe pitches) of the respective light patterns. The periods of the respective light patterns may be differed. For example, the first light pattern may be specified as a light pattern of a first period (for example, 600 μm), while the second light pattern may be specified as a light pattern of a second period (for example, 800 μm) that is longer than the first period. Combining the first light pattern of the shorter period with the second light pattern of the longer period for measurement achieves both the advantageous effects, i.e., the expanded measurable height range that is the advantage when the second light pattern of the long period is used, and the high accuracy measurement of the high resolution that is the advantage when the first light pattern of the short period is used. As a result, this allows for measurement with high resolution in a wide dynamic range and thereby achieves measurement with the higher accuracy.

A modification may be configured to radiate a light pattern of an identical type (of an identical period) from a plurality of different directions, instead of irradiating one type of light pattern from one direction. For example, a modification may be configured to include two sets of the first illumination device 4A and the second illumination device 4B that are arranged to be opposed to each other like the above embodiment and place the four imaging devices 4A and 4B at intervals of 90 degrees about the printed circuit board 2.

This modified configuration is, however, likely to generate regions that are irradiated with only one of the first light pattern and the second light pattern.

For example, a modification may be configured to provide two sets of the first imaging device 4A and the second imaging device 4B and arrange the first illumination devices 4A and the second illumination devices 4B alternately at intervals of 90 degrees about the printed circuit board. Accordingly, in this configuration, the two first illumination devices 4A may be arranged to be opposed to each other, and the two second illumination devices 4B may be arranged to be opposed to each other.

This modified configuration minimizes the ratio of generation of regions that are irradiated with only one of the first light pattern and the second light pattern. As a result, this ensures measurement with the higher accuracy.

Although the disclosure has been described with respect to only a limited number of embodiments, those skilled in the art, having benefit of this disclosure, will appreciate that various other embodiments may be devised without departing from the scope of the present invention. Accordingly, the scope of the invention should be limited only by the attached claims.

REFERENCE SIGNS LIST

1 . . . substrate inspection apparatus, 2 . . . printed circuit board, 4A . . . first illumination device, 4Aa . . . first light source, 4Ab . . . first liquid crystal grid, 4B . . . second illumination device, 4Ba . . . second light source, 4Bb . . . second liquid crystal grid, 5 . . . camera, 6 . . . control device, 24 . . . image data storage device, 25 . . . calculation result storage device, 26 . . . set data storage device, A . . . gain, B . . . offset, K . . . proportional constant

What is claimed is:

1. A three-dimensional measurement device comprising:
a first irradiator that comprises:
a first light source; and
a first grid that converts a light from the first light source into a first light pattern having a striped light intensity distribution, and that radiates the first light pattern from a first position toward a measurement object;
a first grid controller that controls transfer or changeover of the first grid to change phases of the first light pattern a first predetermined number of times;
a second irradiator that comprises:
a second light source; and
a second grid that converts a light from the second light source into a second light pattern having a striped light intensity distribution, and that radiates the second light pattern from a second position that is different from the first position toward the measurement object;
a second grid controller that controls transfer and changeover of the second grid to change phases of the second light pattern a second predetermined number of times, wherein the second predetermined number is smaller than the first predetermined number;
a camera that takes an image of reflected light from the measurement object irradiated with the first or the second light pattern; and
an image processor that:
performs one of:
a first imaging process of the first predetermined number of imaging processes performed by radiation of the first light pattern with changing the phases in the first predetermined number of times; and
a second imaging process of the second predetermined number of imaging processes performed by radiation of the second light pattern with changing the phases in the second predetermined number of times; and
subsequently performs the other of the first and the second imaging process without waiting for completion of the transfer or changeover of the first or the second grid involved in the one imaging process, wherein
the image processor further:
performs three-dimensional measurement of the measurement object based on the first predetermined number of image data taken by the first predetermined number of imaging processes performed by radiation of the first light pattern;
performs three-dimensional measurement of the measurement object based on the second predetermined number of image data taken by the second predetermined number of imaging processes performed by radiation of the second light pattern by using:
a relationship between a gain and an offset that is determined according to a predetermined imaging condition; and
a value of the gain or the offset with regard to each pixel on the image data that is determined from a luminance value of the pixel;
obtains a measurement result by using one light pattern of the first and the second light pattern with regard to a region that is measurable by radiation of the one light pattern; and
obtains a measurement result by using the other light pattern of the first and the second light pattern with regard to a region that is not measurable by radiation of the one light pattern.

2. The three-dimensional measurement device according to claim 1, wherein
the relationship between the gain and the offset is a relationship that mutually unequivocally determines the gain and the offset.

3. The three-dimensional measurement device according to claim 2, wherein
when the second predetermined number is equal to 2,
when relative phases of the second light pattern with changing the phase twice are 0 and $\gamma$, respectively, and when luminance values of each pixel in two different image data are $V_0$ and $V_1$, respectively, the image processor calculates a phase θ that satisfies relations of Expressions (1), (2) and (3) given below in three-dimensional measurement:

$$V_0 = A \sin θ + B \quad (1)$$

$$V_1 = A \sin(θ+γ) + B \quad (2)$$

$$A = KB \quad (3)$$

where γ≠0, A denotes the gain, B denotes the offset and K denotes a proportional constant.

4. The three-dimensional measurement device according to claim 3, wherein
γ is equal to 180 degrees.

5. The three-dimensional measurement device according to claim 3, wherein
γ is equal to 90 degrees.

6. The three-dimensional measurement device according to claim 2, further comprising:
a memory that stores information about the relationship between the gain and the offset that is calculated in advance by calibration.

7. The three-dimensional measurement device according to claim 2, wherein
the image processor determines the relationship between the gain and the offset based on the first predetermined number of image data taken by the first predetermined number of imaging processes performed by radiation of the first light pattern.

8. The three-dimensional measurement device according to claim 2, wherein
the image processor determines the relationship between the gain and the offset based on the second predetermined number of image data taken by the second predetermined number of imaging processes performed by radiation of the second light pattern.

9. The three-dimensional measurement device according to claim 1, wherein
the relationship between the gain and the offset is a relationship that gives the gain and the offset proportional to each other.

10. The three-dimensional measurement device according to claim 9, wherein
when the second predetermined number is equal to 2,
when relative phases of the second light pattern with changing the phase twice are 0 and γ, respectively, and
when luminance values of each pixel in two different image data are $V_0$ and $V_1$, respectively,
the image processor calculates a phase θ that satisfies relations of Expressions (1), (2) and (3) given below in three-dimensional measurement:

$$V_0 = A \sin θ + B \quad (1)$$

$$V_1 = A \sin(θ+γ) + B \quad (2)$$

$$A = KB \quad (3)$$

where γ≠0, A denotes the gain, B denotes the offset and K denotes a proportional constant.

11. The three-dimensional measurement device according to claim 1, wherein
when the second predetermined number is equal to 2,
when relative phases of the second light pattern with changing the phases twice are 0 and γ, respectively, and
when luminance values of each pixel in two different image data are $V_0$ and $V_1$, respectively,
the image processor calculates a phase θ that satisfies relations of Expressions (1), (2) and (3) given below in three-dimensional measurement:

$$V_0 = A \sin θ + B \quad (1)$$

$$V_1 = A \sin(θ+γ) + B \quad (2)$$

$$A = KB \quad (3)$$

where γ≠0, A denotes the gain, B denotes the offset and K denotes a proportional constant.

12. The three-dimensional measurement device according to claim 11, wherein
γ is equal to 180 degrees.

13. The three-dimensional measurement device according to claim 11, wherein
γ is equal to 90 degrees.

14. The three-dimensional measurement device according to claim 1, further comprising:
a memory that stores information about the relationship between the gain and the offset that is calculated in advance by calibration.

15. The three-dimensional measurement device according to claim 1, wherein
the image processor determines the relationship between the gain and the offset based on the first predetermined number of image data taken by the first predetermined number of imaging processes performed by radiation of the first light pattern.

16. The three-dimensional measurement device according to claim 1, wherein
the image processor determines the relationship between the gain and the offset based on the second predetermined number of image data taken by the second predetermined number of imaging processes performed by radiation of the second light pattern.

17. The three-dimensional measurement device according to claim 1, wherein
the image processor:
obtains the measurement result by using the first light pattern with regard to the region that is measurable by radiation of the first light pattern; and
obtains the measurement result by using the second light pattern with regard to the region that is not measurable by radiation of the first light pattern.

18. The three-dimensional measurement device according to claim 1, wherein
the first grid controller starts the transfer or changeover of the first grid in the first imaging process, simultaneously with termination of the first imaging process,
the image processor starts the first imaging process simultaneously with termination of the transfer or changeover process of the first grid, and
the image processor performs the second imaging process during the transfer or changeover process of the first grid.

19. The three-dimensional measurement device according to claim 1, wherein
the second grid controller performs at least one of the transfer and changeover of the second grid, simultaneously with the transfer or changeover of the first grid.

20. The three-dimensional measurement device according to claim 1, wherein
the measurement object is either a solder paste printed on a printed circuit board or a solder bump formed on a wafer substrate.

* * * * *